United States Patent [19]
Bathurst et al.

[11] Patent Number: 6,004,579
[45] Date of Patent: Dec. 21, 1999

[54] COMPOSITIONS WHICH INHIBIT APOPTOSIS, METHODS OF MAKING THE COMPOSITIONS AND USES THEREOF

[75] Inventors: Ian C. Bathurst, Kensington; Matthew W. Foehr; John G. Goddard, both of San Francisco; L. David Tomei, Richmond; Philip J. Barr, Oakland, all of Calif.

[73] Assignee: LXR Biotechnology, Inc., Richmond, Calif.

[21] Appl. No.: 08/704,732

[22] PCT Filed: Sep. 13, 1996

[86] PCT No.: PCT/US96/14752

§ 371 Date: Sep. 4, 1997

§ 102(e) Date: Sep. 4, 1997

[87] PCT Pub. No.: WO97/09989

PCT Pub. Date: Mar. 20, 1997

[51] Int. Cl.$^6$ .................................................. A61K 9/127
[52] U.S. Cl. .......................... 424/450; 424/401; 514/75; 514/78; 514/844; 514/863; 514/880; 435/240.2; 435/240.3
[58] Field of Search ..................... 424/450, 401; 514/844, 863, 880, 75, 78; 264/4.1, 4.3; 435/260, 240.1, 240.2, 240.21, 240.24, 240.3, 240.54

[56] References Cited

U.S. PATENT DOCUMENTS

| | | |
|---|---|---|
| 3,365,440 | 1/1968 | Circle et al. . |
| 4,263,286 | 4/1981 | Nakajima et al. . |
| 4,340,586 | 7/1982 | Bekierkunst et al. . |
| 4,372,949 | 2/1983 | Kodane ................................ 424/199 |
| 4,544,545 | 10/1985 | Ryan et al. . |
| 4,695,590 | 9/1987 | Lippman . |
| 4,732,863 | 3/1988 | Tomasi et al. . |
| 4,737,323 | 4/1988 | Martin et al. . |
| 4,746,652 | 5/1988 | Buckalew, Jr. et al. . |
| 4,762,915 | 8/1988 | Kung et al. . |
| 4,793,996 | 12/1988 | Kennedy et al. . |
| 4,818,540 | 4/1989 | Chien et al. . |
| 4,902,502 | 2/1990 | Nitecki et al. . |
| 4,938,961 | 7/1990 | Collins et al. . |
| 4,959,310 | 9/1990 | Brandon et al. . |
| 4,959,353 | 9/1990 | Brown et al. . |
| 5,000,960 | 3/1991 | Wallach . |
| 5,008,050 | 4/1991 | Cullis et al. . |
| 5,045,530 | 9/1991 | Paradies . |
| 5,052,421 | 10/1991 | McMillen . |
| 5,053,327 | 10/1991 | Brandon et al. . |
| 5,089,261 | 2/1992 | Nitecki et al. . |
| 5,100,662 | 3/1992 | Bolcsak et al. . |
| 5,109,113 | 4/1992 | Caras et al. . |
| 5,130,298 | 7/1992 | Cini et al. . |
| 5,140,043 | 8/1992 | Darr et al. . |
| 5,141,751 | 8/1992 | Tomikawa et al. . |
| 5,190,822 | 3/1993 | Nishikawa et al. . |
| 5,213,804 | 5/1993 | Martin et al. . |
| 5,217,717 | 6/1993 | Kennedy et al. . |
| 5,252,348 | 10/1993 | Schreier et al. . |
| 5,258,499 | 11/1993 | Konigsberg et al. . |
| 5,292,499 | 3/1994 | Evans et al. . |
| 5,326,690 | 7/1994 | Xu et al. . |
| 5,330,972 | 7/1994 | Cope . |
| 5,340,568 | 8/1994 | Piazza et al. . |
| 5,374,548 | 12/1994 | Caras . |
| 5,395,619 | 3/1995 | Zalipsky et al. . |
| 5,447,722 | 9/1995 | Lang et al. . |
| 5,449,513 | 9/1995 | Yokoyama et al. . |
| 5,466,782 | 11/1995 | Rossett ..................................... 530/374 |
| 5,480,877 | 1/1996 | Mosher, Jr. et al. . |
| 5,540,925 | 7/1996 | Mikulski et al. . |
| 5,540,935 | 7/1996 | Miyazaki et al. . |
| 5,559,213 | 9/1996 | Hakimi et al. . |
| 5,595,732 | 1/1997 | Hakini et al. . |
| 5,798,091 | 8/1998 | Trevino ................................ 424/9.52 |

FOREIGN PATENT DOCUMENTS

| | | |
|---|---|---|
| 0 036 277 | 9/1981 | European Pat. Off. . |
| 0 047 480 | 3/1982 | European Pat. Off. . |
| 0626177 | 11/1994 | European Pat. Off. . |
| 63-51335 | 3/1988 | Japan . |
| WO 87/00056 | 1/1987 | WIPO . |
| WO 90/03574 | 4/1990 | WIPO . |
| WO 92/19267 | 11/1992 | WIPO . |
| WO 94/13311 | 6/1994 | WIPO . |
| WO 94/20121 | 9/1994 | WIPO . |
| WO 94/25621 | 11/1994 | WIPO . |
| WO 95/15173 | 6/1995 | WIPO . |
| WO 95/32706 | 12/1995 | WIPO . |

OTHER PUBLICATIONS

Aussel et al., "Human alpha–fetoprotein–fatty acid interaction" *Biochem. Biophys. Res. Comm.* (1983) 115:38–45.

Banaszak et al., "Lipid–binding proteins: A family of fatty acid and retinoid transport proteins" *Advances in Protein Chemistry* (1994) 45:89–151.

Bass, "Cellular binding proteins for fatty acids and retinoids: similar or specialize functions?" *Mol. Cell. Biochem.* (1993) 123:191–202.

Belzer et al., "Principles of solid–organ preservation by cold storage" *Transplantation* (1988) 45:673–676.

Buerke et al., "Cardioprotective effect of insulin–like growth factor I in myocardial ischemia followed by reperfusion" *Proc. Natl. Acad. Sci. USA* (1995) 92:8031–8035.

Burnham, "Polymers for delivering peptides and proteins" *Am. J. Hosp. Pharm.* (1994) 51:210–218.

Collins et al., "New organ preservation solutions" *Kidney International* (1992) 42 (Suppl. 38):S–197–S–202.

Collins et al., Heart preservation solution containing polyethyleneglycol: an immunosuppresive effect? *The Lancet* (1991) 338:890.

Cooper, ed., *The Transplantation and Replacement of Thoracic Organs*, Kluwer Academic Publishers, Dordrecht (1997). A title page and table of contents are included herewith.

(List continued on next page.)

Primary Examiner—Gollamudi S. Kishore
Attorney, Agent, or Firm—Sheridan Ross P.C.

[57] ABSTRACT

The present invention provides compositions that inhibit apoptosis, methods for making the compositions, and methods of use thereof.

46 Claims, 15 Drawing Sheets

OTHER PUBLICATIONS

Delgado et al., "The uses and properties of PEG–linked proteins" *Crit. Rev. Ther. Drug. Carrier Sys.* (1992) 9:249–304.

Donovan et al., "The cellular retinoic acid binding proteins" *J. Steroid Biochem. Mol. Biol.* (1995) 53:459–465.

Elorza et al., "Comparison of particle size and encapsulation parameters of three liposomal preparations" *J. Microencapsulation* (1993) 10:237–248.

Fex et al., "Studies of the spontaneous transfer of retinol from the retinol: retinol–binding protein complex to unilamellar liposomes" *Biochim. Biophys. Acta* (1987) 901:255–264.

Flower, "The lipocalin protein family:structure and function" *Biochem. J.* (1996) 318:1–14.

Fordyce et al., "Studies on reactions relating to carbohydrates and polysaccharides. LVI. The synthesis of the higher polyoxyethylene glycols" *J. Am. Chem. Soc.* (1939) 61:1905–1910.

Fox, "Reperfusion injury: laboratory phenomenon or clinical reality?" *Cardiovasc. Res.* (1992) 26:656–659.

Friede et al., "Selective induction of protection against influenza virus infection in mice by a lipid–peptide conjugate delivered in liposomes" *Vaccine* (1994) 12:791–797.

Geisow et al. "Structures and functions of a supergene family of calcium and phospholipid binding proteins" *Prog. Clin. Biol. Res.* (1990) 349:111–121.

Ghosh et al., "Targeting of liposomes to hepatocytes" *Liver Diseases, Targeted Diagnosis and Therapy Using Specific Receptors and Ligands* (1991) Wu et al., ed., Marcel Dekker, New York, pp. 87–103.

Glatz et al., "Intracellular transport of lipids" *Mol. Cell. Biochem.* (1989) 88:37–44.

Gossett et al., "Acyl–CoA binding proteins: Multiplicity and function" *Lipids* (1996) 31:895–918.

Gottlieb et al., "Reperfusion injury induces apoptosis in rabbit cardiomyocytes" *J. Clin. Invest.* (1994) 94:1621–1628.

Gregoriadis, ed., *Liposomes as Drug Carriers: Recent Trends and Progress* (1988) John Wiley & Sons, New York. A title page and table of contents are included herewith.

Gregoriadis, *Liposome Technology 2nd Edition Volume I: Liposome Preparation and Related Techniques* (1993) CRC Press, Boca Raton. A title page and table of contents are included herewith.

Hamilton et al., "Locations of the three primary binding sites for long–chain fatty acids on bovine serum albumin" *Proc. Natl. Acad. Sci. USA* (1991) 88:2051–2054.

Ishihara, "Preparation of asialofetuin–labeled liposomes with encapsulated human interferon–γ and their uptake by isolated rat hepatocytes" *Pharm. Res.* (1990) 7:542–546.

Itasaka et al., "Modification of rejection of polyethylene glycol in small bowel transplantation" *Transplantation* (1994) 57:645–648.

Itoh et al., "DNA fragmentation of human infarcted myocardial cells demonstrated by the nick end labeling method and DNA agarose gel electrophoresis" *Am. J. Pathol.* (1995) 146:1325–1331.

Karmazyn, "Ischemic and reperfusion injury in the heart. Cellular mechanisms and pharmacological interventions" *Can. J. Physiol.* (1991) 69:719–730.

Kerr et al., "Apoptosis: A basic biological phenomenon with wide–ranging implications in tissue kinetics" *Br. J. Cancer* (1972) 26:239–257.

Kimelberg et al., "Interactions of basic proteins with phospholipid membranes" *J. Biol. Chem.* (1971) 246:1142–1148.

Laukkanen et al., "Functional immunoliposomes harboring a biosynthetically lipid–tagged single–chain antibody" *Biochem.* (1994) 33:11664–11670.

Majerus et al., "Acyl Carrier Protein. VII. The primary structure of the substrate–binding site" *J. Biol. Chem.* (1965) 240:4723–4726.

Mendz et al., "Interaction of myelin basic protein with micelles of dodecylphosphocholine" *Biochem.* (1984) 23:6041–6046.

Menger, "On the structure of micelles" *Acc. Chem. Res.* (1979) 12:111–117.

Menger, "The bioorganic chemistry of aggregated molecules" *Biorganic Chemistry III. Macro– and Multicomponent Systems* (1977) Van Tanelen, ed., Academic Press, New York. Chapter 7, pp. 137–151.

Mittal, ed., *Micellization, Solubilization, and Microemulsions* (1977) Plenum Press, New York. A title page and table of contents are included herewith.

Mittal, ed., *Solution Chemistry of Surfactants* (1979) Plenum Press, New York. A title page and table of contents are included herewith.

Núñez et al., "Bcl–2 and Bcl–x: regulatory switches for lymphoid death and survival" *Immunol. Today* (1994) 15:582–588.

Nussbaum et al., "Reconstitution of functional influenza virus envelopes and fusion with membranes and liposomes lacking virus receptors" *J. Virol.* (1987) 61:2245–2252.

Powell, III, "Polyethylene glycol" *Handbook of Water–Soluble Gums & Resins* (1980) R.L. Davidson, ed., McGraw–Hill, New York, Chapter 18, pp. 18–1–18–31.

Puyal et al., "Design of a short membrane–destabilizing peptide covalently bound to liposomes" *Biochim. Biophys. Acta* (1994) 1195:259–266.

Rakowska et al., "A fusogenic protein from rat brain microsomal membranes: Partial purification and reconstitution into liposomes" *J. Membrane Biol.* (1994) 142:35–42.

Rothwell et al., "Involvement of cytokines in acute neurodegeneration in the CNS" *Nuerosci. Biobehav. Rev.* (1993) 17:217–227.

Rubas et al., "Incorporation of the reovirus M cell attachment protein into small unilamellar vesicles: incorporation efficiency and binding capability to L929 cells in vitro" *J. Microencapsulation* (1990)7:385–395.

Singer, "Effect of different drugs on a cytochrome c–phospholipid bilayer membrane" *Can. J. Physiol.* (1978) 56:555–563.

Stavridis et al., "Construction of transferrin–coated liposomes for in vivo transport of exogenous DNA to bone marrow erythroblasts in rabbits" *Exp. Cell Res.* (1986) 164(2):568–572.

Tokunaga et al. "The immunosuppressive effect of polyethylene glycol in a flush solution for rat liver transplantation"(1992) *Transplantation* (1992) 54:756–758.

Tranum–Jensen et al., "Membrane topology of insulin receptors reconstituted into lipid vesicles" *J. Membrane Biol.* (1994) 140:215–223.

Umansky et al., "Post–ischemic apoptotic death of rat neonatal cardiomyocytes" *Cell Death and Differentiation* (1995) 2:235–241.

Umansky et al., "Dog cardiomyocyte death induced in vivo by ischemia and reperfusion" *Basic and Applied Myology* (1996) 6:227–235.

Van et al., "Bilayer structure in phospholipid–cytochrome c model membranes" *J. Membrane Biol.* (1975) 20:155–170.

Vancura et al., "Regulation of mitochondrial and microsmal phospholipid synthesis by liver fatty acid–binding protein" *J. Biol. Chem.* (1992) 267:14353–14359.

Vaux et al., "The molecular biology of apoptosis" *Proc. Natl. Acad. Sci. USA* (1996) 93:2239–2244.

Vemuri et al., "Preparation and characterization of liposomes as therapeutic delivery systems: a review" *Pharm. Acta Helvetiae* (1995) 70:95–111.

Walther et al. "Uptake of antioxidants in surfactant liposomes by cultured alveolar type II cells is enhanced by SP–A" *Am. J. Physiol.* (1993) 265:L330–339.

Watwe et al., "Manufacture of liposomes: A review" *Curr. Sci.* (1995) 68:715–724.

Whyte, "ICE/CED–3 proteases in apoptosis" *Trends in Cell Biol.* (1996) 6:245–248.

Wicomb et al., "Value of polyethylene glycol (PEG) and horseradish peroxidase (HRP) for hypothermic rabbit heart perfusion" *Transplantation Proceedings* (1989) 21:1366–1368.

Wicomb et al., "Optimal cardioplegia and 24–hour heart storage with simplified UW solution containing polyethylene glycol" *Transplantation* (1990) 49:261–264.

Wicomb et al., "Forty–eight hours hypothermic perfusion storage of pig and baboon hearts" *J. Surg. Res.* (1986) 40:276–284.

Wicomb et al., "Comparison of cardioplegic and UW solutions for short–term rabbit heart preservation" *Transplantation* (1989) 47:733–734.

Wicomb et al., "24–hour rabbit heart storage with UW solution" *Transplantation* (1989) 48:6–9.

Wicomb et al., "Twenty–four –hour ice storage of rabbit heart" *J. Heart Lung Transplantation* (1994) 13:891–894.

Woodle et al., "Sterically stabilized liposomes" *Biochim. Biophys. Acta* (1992) 1113:171–199.

Yachnin et al., "Lipid interactions with human alpha–fetoprotein (AFP). A study of the role of such interactions in the ability of human AFP to suppress lymphocyte transformation" *Oncodev. Biol. Med.* (1980) 1:273–285.

Zalipsky et al., "Long circulating, cationic liposomes containing amino–PEG–phosphatidylethanolamine" *FEBS Letters* (1994) 353:71–74.

Wyllie, "Glucocorticoid–induced thymocyte apoptosis is associated with endogenous endonuclease activation" *Nature* (1980) 284:555–556.

Kanter et al., "Epidermal growth factor and tumor promoters prevent DNA fragmentation by different mechanisms" *Biochem. Biophys. Res. Comm.* (1984) 118:392–399.

Duke et al., "IL–2 addiction: Withdrawal of growth factor activates a suicide program in dependent T cells" *Lymphokine Res.* (1986) 5:289–299.

Tomei et al., "Inhibition of radiation–induced apoptosis in vitro by tumor promoters" *Biochem. Biophys. Res. Comm.* (1988) 155:324–331.

Kruman et al., "Apoptosis of murine BW 5147 thymoma cells induced by dexamethasone and γ–irradiation" *J. Cell. Physiol.* (1991) 148:267–273.

Ameisen et al., "Cell dysfunction and depletion in AIDS: the programmed cell death hypothesis" *Immunol. Today* (1991) 12:102–105.

Sheppard et al., "The relationship between AIDS and immunologic tolerance" *J. Acquired Immune Deficiency Syndromes* (1992) 5:143–147.

Gerschenson et al., "Apoptosis: A different type of cell death" *FASEB J.* (1992) 6:2450–2455.

Cohen et al., "Apoptosis and programmed cell death in immunity" *Ann. Rev. Immunol.* (1992) 10:267–293.

Tomei et al., *Apoptosis The Molecular Basis of Cell Death* (1991) Cold Spring Harbor Laboratory Press. The title page and table of contents are included herewith.

Troll et al., "Anticarcinogenic action of protease inhibitors" *Dept. of Envir. Med., New York Univ. Med. Ctr.,* New York, NY 10016, pp. 265–282, 1992.

Birk, "The Bowman–Birk inhibitor" *J. Peptide Protein* (1985) 25:113–131.

Chou et al., "Non–selective inhibition of transformed cell growth by a protease inhibitor" *Proc. Natl. Acad. Sci. USA* (1974) 71:1748–1752.

Yavelow et al., "Nanomolar concentrations of Bowman–Birk soybean protease inhibitor suppress x–ray induced transformation in vitro" *Proc. Natl. Acad. Sci. USA* (1985) 82:5395–5399.

Yavelow et al., "Bowman–Birk soybean protease inhibitor as an anticarcinogen" *Cancer Research* (1983) 43:2454s–2459s.

Kennedy, "Prevention of carcinogenesis by protease inhibitors" *Cancer Res.* (1994) (Suppl) 54:1999s–2005s.

Moolenaar, "LPA: A novel lipid mediator with diverse biological actions" *TICB* (1994) 4:213–219.

Eichholtz et al., "The bioactive phospholipid lysophosphatidic acid is released from activated platelets" *Biochem. J.* (1993) 291:677–680.

Moolenaar, "Lysophosphatidic acid, a multifunctional phospholipid messenger" *J. Biol. Chem.* (1995) 270:12949–12952.

Bligh et al., "A rapid method of total lipid extraction and purification" *Can. J. Biochem. Physiol.* (1959) 37:911–917.

Patton et al., "Separation of phospholipids and individual molecular species of phospholipids by high–performance liquid chromatography" *J. Lipid Res.* (1982) 23:190–196.

Jungalwala, "Recent developments in techniques for phospholipid analysis" *Phospholipids in Nervous Tissues* (1985) Eichberg, ed., John Wiley and Sons. pp. 1–44.

Hamilton et al., *Lipid Analysis. A Practical Approach* (1992) Rickwood et al. eds., IRL Press at Oxford University Press. The title page, preface and table of contents are included herewith.

Kates, "Techniques of lipidology: Isolation, analysis and identification of lipids" *Laboratory Techniques in Biochemistry and Molecular Biology* (1986) Burdon et al. eds., Elsevier.

Singal, *Oxygen Radicals in the Pathophysiology of Heart Disease* (1988) Kluwer Academic Publishers, MA. The title page and table of contents are included herewith.

Stenn et al., "Expression of the bcl–2 protooncogene in the cycling adult mouse hair follicle" *J. Invest. Dermatol.* (1994)103:107–111.

Oates et al., "Cell death (apoptosis) during pancreatic involution after raw soya flour feeding in the rat" *Am. J. Physiol.* (1986) 250:69–614.

Ashagbley et al., "Synthesis of ether–linked analogues of lysophosphatidate and their effect on the proliferation of human epithelial cancer cells in vitro" *Anticancer Research* (1996) 16:1813–1818.

Rajasekharan et al., "Use of photoreactive substrates for characterization of lysophosphatidate acyltransferases from developing soybean cotyledons" *Archives of Biochemistry and Biophysics* (1994) 311:389–394.

Tokumura et al., "Cardiovascular effects of lysophosphatidic acid and its structural analogs in rats" *Journal of Pharmacology and Experimental Therapeutics* (1981) 219:219–224.

Tokumura et al., "Gas chromatographic/mass spectrometric analyses of ether–linked lysophosphatidic acid and its analogues" *Biomedical and Environmental Mass Spectrometry* (1986) 13:175–180.

Boggs et al., "Lysophosphatidylcholine attenuates the cytotoxic effects of the antineoplastic phospholipid 1–0–octadecyl–2–0–methyl–rac–glycero–3–phosphocholine" *J. Biol. Chem.* (1995) 270:11612–11618.

Murakami–Murofushi et al., "Stimulation of actin polymerization by physarum–derived novel lysophosphatidic acid, PHYLPA, and its effect on apoptosis of endotherial cells" *Cell Structure and Function* (1994)19(6):483. Abstract No. 28/32.

COMPOSITIONS WHICH INHIBIT APOPTOSIS, METHODS OF MAKING THE COMPOSITIONS AND USES THEREOF

This application is 371 of PCT/US96/14752 filed Sep. 13, 1996.

FIELD OF INVENTION

This invention relates to compositions of matter which are effective in inhibiting apoptotic cell death. More specifically, it relates to compositions of phospholipids (PA, PI, LPA, LPI and LPC) the mixture of which exhibits anti-apoptotic activity.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging.

Recent studies of apoptosis have implied that a common metabolic pathway leading to apoptosis may be initiated by a wide variety of signals, including hormones, serum growth factor deprivation, chemotherapeutic agents, ionizing radiation, and infection by human imnnunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; Kruman et al. (1991) *J. Cell. Physiol.* 148:267–273; Ameisen and Capron (1991) *Immunol. Today* 12:102–105; and Sheppard and Ascher (1992) *J. AIDS* 5:143–147. Agents that affect the biological control of apoptosis thus have therapeutic utility in numerous clinical indications.

Apoptotic cell death is characterized by cellular shrinkage. chromatin condensation, cytoplasmic blebbing, increased membrane permeability and internucleosomal DNA cleavage. Gerschenson et al. (1992) *FASEB J.* 6:2450–2455; and Cohen and Duke (1992) *Ann. Rev. Immunol.* 10:267–293.

A variety of food supplements containing, in part, partially processed plant extracts have been used to ameliorate the gastrointestinal disorders that often accompany chemotherapy, radiation and AIDS. The supplements generally contain carbohydrates, fat and plant protein hydrolysates. See, e.g., Tomei and Cope et al. in Apoptosis The Molecular Basis of Cell Death (1991) Cold Spring Harbor Laboratory Press.

Several proteinase inhibitors derived from plant extracts have anticarcinogenic activity. Troll et al. (1987) *Adv. Cancer Res.* 49:265–283. The Bowman-Birk inhibitors are the best described of these inhibitors. Birk (1985) *Int. J. Pep. Pro. Res.* 25:113–131. Bowman-Birk inhibitors are described as a family of disulfide bonded proteins with a molecular weight of about 8 kD which suppress cellular transformation. Chou et al. (1974) *Proc. Natl. Acad. Sci. USA* 71:1748–1752; Yavelow et al. (1985) *Proc. Natl. Acad. Sci. USA* 82:5395–5399; and Yavelow et al. (1983) *Cancer Res.* (Suppl.) 43:2454s–2459s. Crude soybean extracts containing Bowman-Birk inhibitors have been described. Kennedy et al. U.S. Pat. No. 4,793,996; PCT publication No. WO 94/20121; and Kennedy, A. R. (1994) *Cancer Res.* (Suppl) 54: 1999s–2005s. Bowman-Birk inhibitors have also been described immunologically. WO 90/03574; and U.S. Pat. Nos. 4,959,310; and 5,053,327. Bowman-Birk inhibitors have also been found to have activity in degranulation of macrophages. Japanese Patent No. 63051335.

Phospholipids are a class of amphipathic phosphorous-containing lipids which are essential constituents of biological membranes. Various phospholipid preparations have been used for cooking, drug delivery (liposomes), slow release delivery systems, carrier media for hydrophobic drugs, gene transfer and replacement therapy, sunscreens, emulsions, anti-foaming agents, replacement of damaged or absent pulmonary surfactants, detergents and membrane stabilization.

Phosphatidic acid (PA), phosphatidylinositol (PI), lysophosphatidic acid (LPA), lysophosphatidylinositol (LPI), and lysophosphatidylcholine (LPC) are found in a variety of plant and animal products. LPA is found in a variety of plant and animal products and has been reported to have a variety of physiological activities including mitogenesis, growth factor and to be an anmi-wrinkle agent. U.S. Pat. Nos. 4,263,286; 4,746,652; 5,326,690; and 5,340,568. LPA is reviewed in detail by Moolenaar (1994) *TICB* 4:213–219; and Eichholtz et al. (1990) *Biochem. J.* 291:677–680; and Moolenaar (1995) *J. Biol. Chem.* 270:12949–12952.

PCT Publication No. WO 95/15173 describes plant-derived delipidated extracts that produce an anti-apoptotic effect. It has now been found that these extracts contain LPA, LPC, LPI, PA and PI in the ratios 2:1:2:20:20, by weight in addition to various protein and carbohydrate constituents.

All references cited herein are incorporated by reference in their entirety.

SUMMARY OF THE INVENTION

The present invention encompasses compositions that inhibit apoptosis and methods of making these compositions. The invention also encompasses methods of making and using these compositions.

Accordingly, one aspect of the invention is a composition comprising the phospholipids phosphatidic acid (PA), phosphatidylinositol (PI), lysophosphatidic acid (LPA), lysophatidylinositol (LPI) and lysophosphatidylcholine (LPC), with the phospholipids in anti-apoptotic ratios.

In another aspect, methods are provided for making these compositions. These methods include combining an effective amount of the above phospholipids in their respective ratios and sonicating these phospholipids until the solution achieves optical clarity.

In another aspect, methods of using these compositions are provided. These methods include using these compositions for treatment of apoptosis by administration of a therapeutically effective amount of a pharmaceutically acceptable agent containing the composition to a patient in need of such treatment. The methods include making a composition for treatment of conditions related to apoptosis. Other methods using these compositions include preventing apoptosis in cultured cells, methods of increasing organ preservation for subsequent organ transplantation and in situ preservation for bypass operations, e.g., heart, liver, lungs, brain, etc., and methods of treating dermatologic conditions in which apoptosis is implicated.

MODES FOR CARRYING OUT THE INVENTION

Figure 1A:
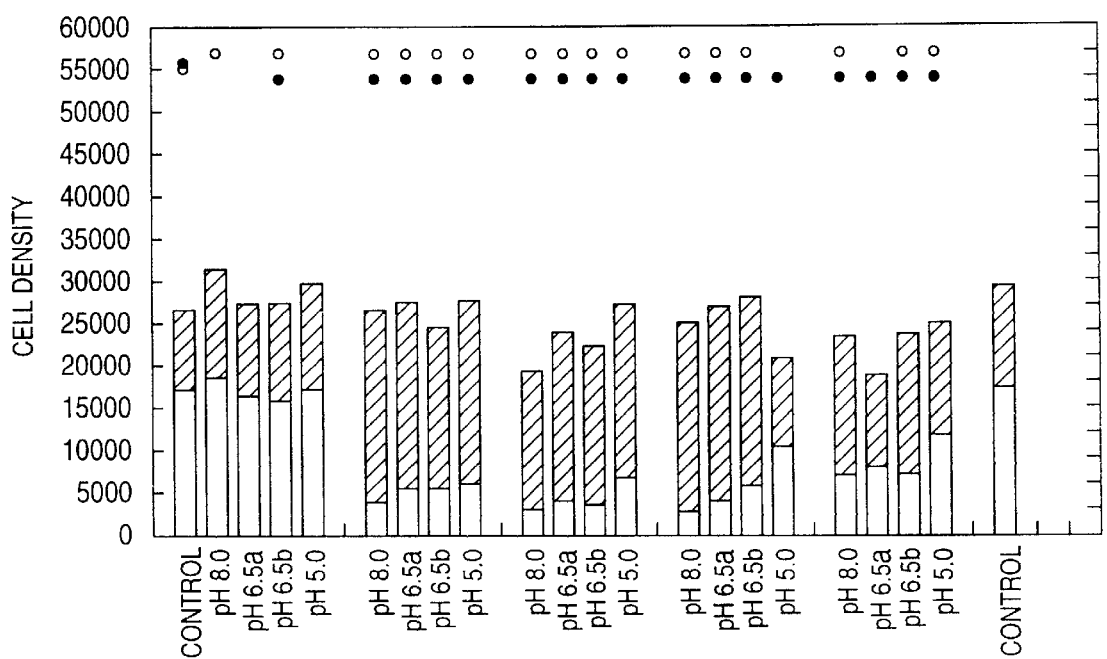
FIGS. 1(A) and 1(B) are bar graphs depicting stability of Elirex™ (formerly termed "ROM") when stored for one week at various temperatures. The hatched portion of the bar represents live adherent cells (ADH). The solid portion of the bar represents apoptotic, serum deprived, released cells (SDR). Stability is expressed in terms of cell density (FIG. 1(A)) and percentage (FIG. 1(B)). For FIG. 1(A), open circles denote statistically significant increases in adherent cells; solid circles denote statistically significant decreases in apoptotic cells. For FIG. 1(B), open diamonds denote statistically significant percentages of cells saved; solid diamonds denote statistically significant percentages of apoptotic cells.

It has now been found that compositions containing certain ratios of five phospholipids found in plants and animals or made synthetically, significantly enhance anti-apoptotic activity compared to naturally occurring ratios of these phospholipids. These compositions are readily obtainable from a variety of sources, including plants and animals. The compositions may also be prepared synthetically by methods known in the lipid synthesis art. The compositions may vary slightly in chemical constituents depending on the source and growing conditions of the plant from which they are derived. The compositions are referred to herein as Elirex™.

We previously described an extract derived from plants capable of producing an anti-apoptotic effect as measured in in vitro cell assays designed to respond to an apoptosis signal. PCT WO 95/15173. We have now found that the active ingredients are the phospholipids phosphatidic acid (PA); phosphatidylinositol (PI); lysophosphatidic acid (LPA); lysophosphatidylinositol (LPI); and lysophosphatidylcholine (LPC). The naturally derived extracts have these phospholipid components in the ratio of approximately 20:20:2:1:2, respectively. This is referred to herein as "native mixture" (NM). These phospholipids can be recombined at these ratios to obtain reconstituted native mixture (RNM) which lacks the contaminants found in the native mixture. RNM is considered to be an embodiment of Elixir™. Although this is the standard ratio most commonly found, it may vary within narrow ranges depending on various parameters, including but not limited to, season, growth conditions, growth region, harvest conditions, storage, type of seed (breed) and genetic engineering of the seeds. The present invention is a different, much more effective, ratio of these phospholipids than the ratio found from native sources.

The compositions of the invention comprise as an active component, the phospholipids PA; PI; LPA; LPI; and LPC. The phospholipids are present in a range of ratios from 0–20:5–20:2–16:0–4:0–8, respectively. Preferably, these phospholipids are in a ratio of approximately 2–15:8–15:6–10:2–4:2–8, respectively. Most preferably, these phospholipids are in a ratio of approximately 10:10:8:2:4, respectively. Although the phospholipid structures are well defined, they may vary with respect to lipid chain length and saturation. Typically, the phospholipids have the following structures but may include other structures known in the art provided they are effective in producing an anti-apoptotic response in any standard apoptosis assay.

PA has the structure:

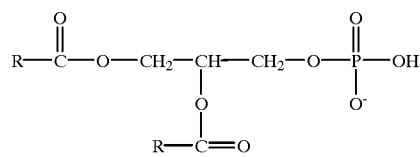

PI has the structure:

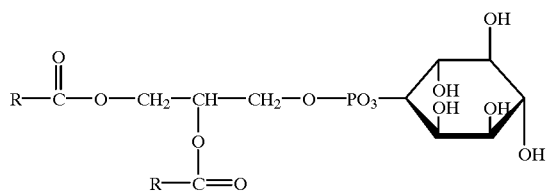

LPA has the structure:

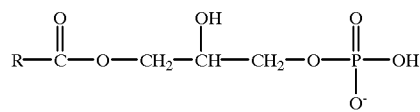

wherein R is an unsubstituted or substituted, saturated or unsaturated, straight or branched chain alkyl having from 11 to about 23 carbon atoms.

Also, as used herein, LPA encompasses a variety of molecules, including, but not limited to, a 2-deoxy- or 2-deoxy-2-halo-lysophosphatidic acid compound having the structure:

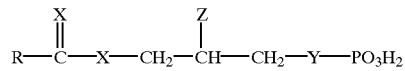

or a pharmaceutically-acceptable salt thereof, wherein R is unsubstituted or substituted, saturated or unsaturated, straight or branched-chain alkyl having from 11 to about 23 carbon atoms; each X is independently O or S; Y is O or $(CH)_n$ where n=0–2; and Z is H, halo, $NH_2$, SH, OH, or $OPO_3H_2$.

Also included is RC(O)O being lauryl, myristoyl, palmityl, stearyl, palmitoleyl, oleyl or linoleyl; more particularly, oleyl, palmitoleyl, myristyl, palmityl, or lauryl. Particularly preferred are 16 carbon chain palmitoyl and palmitoleoyl and 18 carbon chain stearoyl, oleoyl and linoleoyl, for example, but not excluding fatty acids of other carbon lengths including, but not limited to, C12, C14, C20 and C22. For a representative example of suitable phospholipids see any chemical catalog of a phospholipid supplier, for instance, the (1994) Avanti catalog, particularly pages 14 and 21.

LPI has the structure:

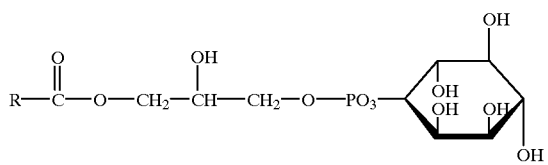

wherein R is an unsubstituted or substituted, saturated or unsaturated, straight or branched chain alkyl having from 11 to about 23 carbon atoms.

LPC has the structure:

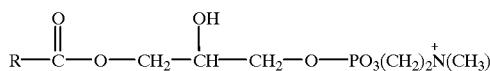

wherein R is an unsubstituted or substituted, saturated or unsaturated, straight or branched chain alkyl having from 11 to about 23 carbon atoms.

Pharmaceutically-acceptable salts of the phospholipids, include, but are not limited to, the free acid form, alkali metal salts, such as sodium and potassium; alkaline earth metal salts, such as calcium and magnesium; non-toxic heavy metal salts; ammonium salts; trialkylammonium salts, such as trimethylamunonium and triethylammonium; and alkoxyamrnmonium salts, such as triethanolammonium, tri (2-hydroxyethyl)ammonium, and tromethamine (tris (hydroxymethyl)aminomethane). Particularly preferred are sodium and ammonium salts.

The phospholipids of the composition can be obtained from commercial sources or can be isolated from a variety of different plants (including plant organs) and animals. Preferably the plants are in the soybean family, but the phospholipids can be isolated from other plants including, but not limited to, those in the *leguminosae* (beans and peas etc.). The phospholipids can also be isolated from partially purified plant extracts including, but not limited to, soy molasses, lecithin, partially purified protein concentrates, partially purified protein hydrolysates and other soy fractions from which lipid can be extracted. It is within the skill of one in the art, utilizing the methods described herein, to determine whether the phospholipids of the present invention can be isolated from a particular species of plant, plant extract or organ within a plant. U.S. Pat. No. 3,365,440 describes extraction of lipids from soybeans.

Any plant extract or part thereof that yields the phospholipids of the compositions is suitable for use in the present invention. The plant organs which can be utilized include, but are not limited to, stems, leaves, roots, flowers, rhizomes, and preferably, storage organs such as seeds, tubers and bulbs. Preferably, the plant part utilized is a storage organ. Most preferably the dried seeds of soybeans are used. Although the terms "seed" and "seeds" are used herein, it should be understood that these terms encompass any plant part which yields at least one phospholipid of the invention.

The phospholipids can be obtained from the plant sources by any method known in the art provided it results in purification of at least one of the phospholipids of the invention. A variety of methods are known in the art for purifying and analyzing phospholipids from plant sources. For review, see Bligh and Dyer (1959) *Can. J. Biochem. Physiol.* 37:911–917; Patton et al. (1982) *J. Lipid Res.* 23:190–196; Jungalwala (1985) Recent Developments in Techniques for Phospholipid Analysis, in Phospholipids in Nervous Tissues (ed. Eichberg) John Wiley and Sons, pp. 1–44; Hamilton et al. (1992) in the series, A Practical Approach (Rickwood et al. eds.) IRL Press at Oxford University Press; and Kates (1986) Techniques of Lipidology: Isolation, Analysis and Identification in Laboratory Techniques in Biochemistry and Molecular Biology (Burdon et al. eds.) Elsevier.

Phospholipids can also be derived from animal sources. Preferably, the animal is a mammal. Even more preferably, the phospholipids are derived from liver cells. Such phospholipids are commercially available or can be purified from animal tissue by methods known in the art, for instance from animal and egg lecithin or from the compositions described in WO 95/15173.

The phospholipids of the invention can also be synthesized by methods known in the art. Suitable semi-synthetic phospholipids and their synthesis are described in Kates, Techniques of Lipidology (1972).

Various degrees of purity of the phospholipids can be used. Purity can be assayed by any method known in the art such as two dimensional TLC or HPLC and assayed for total lipids, phospholipids or phosphate. Various suitable methods are outlined in Kates (1972). Preferably, the phospholipids must be of sufficient purity such that, when mixed at a total concentration of about 10 mg/ml, the mixture can be sonicated as described below to provide a relatively translucent solution. Preferably, the phospholipids are at least 90% pure, more preferably, they are at least 95% pure and, most preferably, they are at least 99% pure.

The phospholipids can be used with or without binding proteins. As used herein, a "binding protein" is any protein that will protect LPA to preserve its activity. Examples of binding proteins include, but are not limited to, albumins such as bovine serum albumin (BSA) and pea albumin.

Other factors which may influence the activity of the Elirex™ compositions are chain length of the phospholipids, the degree of saturation, presence of cholesterol, presence of micelles, liposomes, detergents, and emulsifying agents, and chain position in LPA, i.e., first or second carbon on the glycerol. While not being bound to any one theory, sonication may cause the formation of liposomes and/or micelles or other multilamellar vesicles which may enhance activity of the Elirex™. Short chain LPA is not as effective as C16 and C18 varieties.

Without being bound by any one theory, it is hypothesized that the presence of PA, PI, LPI and LPC protect LPA from degradation and may potentiate the physiological effects of LPA.

The invention further includes methods of making the Elirex™ compositions. The phospholipids (PA:PI:LPA:LPI:LPC) are present in a range of ratios from 0–20:5–20:2–16:0–4:0–8, respectively. Preferably, these phospholipids are in a ratio of approximately 2–15:8–15:6–10:2–4:2–8, respectively. The preferred composition is where phospholipids are combined in a ratio of about 10:10:8:2:4 by weight. A ratio of "about" means that the ratios of the phospholipids can range approximately up to 15% but preferably not more than 5%. More preferably, the ratios are within ±0.5%.

The phospholipids can be suspended in any buffered solution that is preferably free of divalent cations having a pH range of 5 to 8, such as D-PBS (phosphate buffered saline, free of calcium and magnesium salts; GibcoBRL) or 50 mM ammonium bicarbonate containing isotonic sodium chloride. When the compositions are to be used therapeutically, the buffered solution is preferably physiologically acceptable. A wide range of pH values are effective. Preferably the pH is between 5.5–8 although, any pH at which the Elirex™ is at least minimally effective is suitable for use. The mixture has been found to be most active at pH 8. Preferably, the phospholipids are suspended in 50 mM ammonium bicarbonate in 0.154 M sodium chloride, with a pH of 7.7–8.0.

Preferably, the mixture of phospholipids is disrupted in order to achieve maximal activity. Any method of disruption including, but not limited to, microfluidization, extrusion and sonication may be used, provided that it does not denature or otherwise chemically modify the phospholipids. Typically the mixture is sonicated until optical clarity is attained although sonication can be continued beyond this point provided the mixture is not overheated. The preferred sonication parameters are those provided in the examples herein. As used herein, "optical clarity" indicates that the mixture changes from opaque to translucent. This change is readily monitored visually; no further measurements are necessary. However, "translucent" can be defined as when the mixture has an O.D. 600 of less than about 0.2 AU.

Concentrations of up to approximately 50 mg/ml can be prepared. Preferably, 10 mg/ml solutions are used. Typically, sonication is in 5 minute alternating cycles, with 5 minutes of sonication followed by 5 minutes of equilibration. However, this can be varied, depending on the volume of mixture being sonicated and the heat generated by sonication.

The total length of sonication depends on the concentration and volume of the mixture being sonicated and the power output of the sonicator. Sonication should proceed until the mixture has become translucent. Typically, mixtures are sonicated for 3 to 90 minutes. Preferably, sonication proceeds by several periods of 5 minutes each, 6 to 12 total periods, with 1 to 5 minutes between each period to allow equilibration and dissipation of heat. The temperature of the water bath should not exceed about 60° C.; however, the mixtures can be autoclaved without significant loss of activity. Preferably, the temperature of the water bath is not allowed to exceed 37° C. Preferably, the sonicated mixture is passed through a sterile filter before use.

The activity of Elirex™ can be measured in many anti-apoptosis assays known in the art. These include, but are not limited to, the serum deprivation of the C3H/10T1/2 cell assay described in detail in commonly owned PCT Publication No. WO 94/25621 which is the preferred assay method, as well as the methods described in Example 3. Furthermore, in vivo apoptosis inhibition may be measured by any method known in the art.

The invention further comprises therapeutic compositions comprising substantially purified Elirex™. The level of purity necessary for the composition can be determined empirically and is within the skill of one in the art. The compositions are suitable for use in a variety of disorders, as described below, and in both human and veterinary applications.

In general, Elirex™ compositions are pharmaceutically acceptable due to their low toxicity in the therapeutic dosage range, stability and ability to be incorporated into a wide variety of vehicles for numerous routes of administration. Elirex™ can be administered alone or in combination with other pharmaceutically effective agents including, but not limited to, antibiotics, wound healing agents, antioxidants and other therapeutic agents. Suitable antibiotics include, but are not limited to, ampicillin, tetracycline, chloramphenicol and penicillin. Suitable wound healing agents include, but are not limited to, transforming growth factors (TGF-βs), epidermal growth factors (EGFs), fibroblast growth factors (FGFS) and platelet-derived growth factors (PDGFs). Suitable antioxidants include, but are not limited to, Vitamins C and E.

The compositions contain at least a therapeutically effective amount of at least one Elirex™ and may contain at least one physiologically acceptable carrier. A physiologically acceptable carrier is one that does not cause an adverse physical reaction upon administration and one in which Elirex™ are sufficiently soluble to deliver a therapeutically effective amount of the compound. The therapeutically effective amount of Elirex™ depends in part upon the manner of introduction and the indication to be treated and other criteria evident to one of ordinary skill of one in the art. Typically, a therapeutically effective amount is one sufficient to modulate apoptosis in the condition being treated as evidenced by amelioration of the symptoms. Typically, a therapeutically effective amount is from about 0.0001% or 1 $\mu$g/ml by weight of Elirex™ although a wide range of effective amounts may be used for different indications and can be determined empirically. The route(s) of administration useful in a particular indication are discussed below and are well known to one of skill in the art.

Routes of administration include, but are not limited to, topical, transdermal, parenteral, gastrointestinal, transbronchial and transalveolar. Topical administration is accomplished via a topically applied cream, gel, rinse, etc. containing a therapeutically effective amount of Elirex™. Transdermal administration is accomplished by application of a cream, rinse, gel, etc. capable of allowing Elirex™ to penetrate the skin and enter the blood stream. Parenteral routes of administration include, but are not limited to, direct injection such as intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally and direct injection into an airway, such as through a tracheotomy.

While Elirex™ can be topically administered alone, it may be desirable to administer them in a mixture with a topical pharmaceutically or cosmetically acceptable carrier. "Topical pharmaceutically acceptable carrier" as used herein is any substantially non-toxic carrier conventionally usable for topical administration of pharmaceuticals in which the Elirex™ will remain stable and bioavailable when applied directly to skin or mucosal surfaces For example, the Elirex™ can be dissolved in a liquid, dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. The carrier may be a water miscible carrier composition that is substantially miscible in water. Such water miscible topical pharmaceutically acceptable carrier composition can include those made with one or more appropriate ingredients set forth above but can also include sustained or delayed release carriers, including water containing, water dispersible or water soluble compositions, such as liposomes, microsponges, microspheres or microcapsules, aqueous base ointments, water-in-oil or oil-in-water emulsions, gels or the like.

In one embodiment of the invention, the topical pharmaceutically acceptable carrier comprises a sustained release or delayed release carrier. The carrier is any material capable of sustained or delayed release of the Elirex™ to provide a more efficient administration resulting in one or more of less frequent and/or decreased dosage of the Elirex™, ease of handling, and extended or delayed effects on dermatologic conditions. The carrier is capable of releasing Elirex™ when exposed to any oily, fatty, waxy, or moist environment on the area being treated or by difflusing or by release dependent on the degree of loading of Elirex™ to the carrier in order to obtain releases of Elirex™. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Preferably, the sustained or delayed release carrier is a liposome, microsponge, microsphere or gel.

The compositions used in the method of treating dermatologic conditions of the invention are applied directly to the areas to be treated. While not required, it is desirable that the topical composition maintain Elirex™ at the desired location for about 24 to 48 hours.

If desired, one or more additional ingredients conventionally found in topical pharmaceutical or cosmetic compositions can be included with the carrier, such as a moisturizer, humectants, odor modifier, buffer, pigment, preservative, Vitamins such as A, C and E, emulsifier, dispersing agent, wetting agent, odor-modifying agent, gelling agents, stabilizer, propellant, antimicrobial agents, sunscreen, enzymes and the like. Those of skill in the art of topical pharmaceutical formulations can readily select the appropriate specific additional ingredients and amounts thereof. Suitable non-limiting examples of additional ingredients include superoxide dismutase, stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulin, polymucosaccharides, hydroxyethyl starch (such as, DuPont Pentafraction), hyaluronic acids, aloe vera, lecithin, polyoxyethylene sorbitan monooleate, polyethylene glycol, Vitamin A or C, tocopherol (Vitamin E), alpha-hydroxy of alpha-keto acids such as pyruvic, lactic or glycolic acids, or any of the topical ingredients disclosed in U.S. Pat. Nos. 4,340,586, 4,695,590, 4,959,353 or 5,130,298 and 5,140, 043.

Because dermatologic conditions to be treated may be visible, the topical carrier can also be a topical cosmetically acceptable carrier. By "topical cosmetically acceptable carrier" as used herein is meant any substantially non-toxic carrier conventionally usable for topical administration of cosmetics in which Elirex™ will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Thus, to a substantial extent topical cosmetically acceptable carriers and pharmaceutically acceptable carriers are similar, if not often identical, in nature so that most of the earlier discussion on pharmaceutically acceptable carriers also applies to cosmetically acceptable carriers. The compositions can contain other ingredients conventional in cosmetics including perfumes, estrogen, Vitamins A, C or E, alpha-hydroxy or alpha-keto acids such as pyruvic, lactic or glycolic acids, lanolin, vaseline, aloe vera, methyl or propyl paraben, pigments and the like.

The effective amount of the Elirex™ in the compositions used to treat dermatologic conditions or diseases can vary depending on such factors as condition of the skin, age of the skin, the particular ratio of phospholipids or degree of the purity of phospholipids employed, the type of formulation and carrier ingredients used, frequency of administration, overall health of the individual being treated and the like. The precise amount for any particular patient use can be determined by those of skill in the pharmaceutical art taking into consideration these factors and the present disclosure. Preferably the composition is administered in at least two doses and no more than about six doses per day, or less when a sustained or delayed release form is used.

The compositions for topical, oral and parenteral administration usually contain from about 0.001% to about 10% by weight of Elirex™ compared to the total weight of the composition, preferably from about 0.01% to about 2% by weight of Elirex™ to composition, and especially from about 0.1% to about 1.5% by weight of Elirex™ to the composition.

The topical composition is administered by applying a coating or layer to the skin or mucosal area desired to be treated. As a practical matter of convenience, the applied material is rubbed into the area. Applications need not be rubbed into the skin and the layer or coating can be left on the skin overnight.

The present invention provides compositions suitable for transdermal administration including, but not limited to, pharmaceutically acceptable lotions, suspensions, oils, creams, ointments, rinses, gels and liposomal carriers suspended in a suitable vehicle in which a therapeutically effective amount of Elirex™ has been admixed. Such compositions are applied directly to the skin or incorporated into a protective carrier such as a transdermal device (so-called "patch"). Examples of suitable creams, ointments etc. can be found, for instance, in the Physician's Desk Reference. Examples of suitable transdermal devices are described, for instance, in U.S. Pat. No. 4,818,540 (Chien et al.).

The present invention includes compositions of Elirex™ suitable for parenteral administration including, but not limited to, pharmaceutically acceptable sterile isotonic solutions. Such solutions include, but are not limited to, saline and phosphate buffered saline for intravenous, intramuscular, intraperitoneal or subcutaneous injection of Elirex™.

The present invention includes compositions of Elirex™ suitable for gastrointestinal administration including, but not limited to, pharmaceutically acceptable powders, pills or liquids for ingestion and suppositories for rectal administration.

The present invention includes compositions of Elirex™ suitable for transbronchial and transalveolar administration including, but not limited to, various types of pharmaceutically acceptable aerosols for inhalation. An example of a drug administered in the form of an aerosol is pentamidine which is administered to AIDS patients by inhalation to prevent pneumonia caused by *Pneumocystis carnii*.

The present invention further encompasses devices suitable for transbronchial and transalveolar administration of Elirex™. Such devices include, but are not limited to, atomizers and vaporizers. The present invention also includes devices for electrical or direct injection. Electrical injection, or iontophoresis, is the process of using a small electrical current to drive charged elements, compounds and drugs through the skin to deliver the therapeutic compound to the local tissues or to the whole body without breaking the skin.

The present invention encompasses solutions suitable for storage of organs prior to transplantation. Suitable solutions are described in Chien et al. (1993) "Hibernation Induction Trigger for Organ Preservation" in Medical Intelligence Unit, R.G. Landes Co. Austin, Tex. Elirex™ can be used, for instance, to replace and improve on much more impure soy preparations currently in use.

The above-mentioned compositions are meant to describe, but not limit, the compositions suitable for administering Elirex™ of the invention. The methods of producing the various compositions are within the ability of one skilled in the art and are not described in detail here.

The methods of producing suitable devices for injection, topical application, atomizers and vaporizers are known in the art and will not be described in detail.

The invention further provides methods of treating conditions related to apoptosis comprising administering an amount of the Elirex™ effective to inhibit apoptosis. These methods entail administration of a therapeutically effective amount of a pharmaceutically acceptable composition comprising the above-described composition. "Therapeutically effective amount" is an amount sufficient to effect beneficial or desired clinical results. A therapeutically effective amount can be administered in one or more administrations. Various apoptosis-related indications which can be treated, include, but are not limited to, dermatological effects of aging, the effects of reperfusion after an ischemic event, immunosuppression, gastrointestinal perturbations, cardiovascular disorders, rejection of tissue transplantation, wound healing and Alzheimer's disease.

Immunosuppression related disorders are caused by a variety of stimuli which include, but are not limited to, viruses including, but not limited to, HIV, chemotherapeutic agents, and radiation. These stimuli trigger apoptosis in a variety of disorders, including, but not limited to, those of the digestive tract tissues and associated gastrointestinal perturbations.

Gastrointestinal perturbations include, but are not limited to, damage to the lining of the gut, severe chronic ulcers, colitis, radiation induced damage, chemotherapy induced damage, and the perturbation of the gastrointestinal tract caused by parasites, and diarrhea from any other cause. Various viral and bacterial infections are known to result in gastrointestinal perturbations; Elirex™ are also suitable for use in treatment of the side effects associated with these infections. Elirex™ are particularly suited for use in ameliorating the gastrointestinal disturbances associated with chemotherapy. As previously shown, rats treated with methotrexate and phospholipids suffered less feeding problems and had none of the diarrhea found in the control animals. As shown below, the preferred embodiment of Elirex™ has over two hundred percent greater anti-apoptotic activity compared to the naturally derived, impure phospholipid mixture. Thus, Elirex™ are suitable for use not only in preventing the diarrhea associated with chemotherapy but also the nausea.

Elirex™ are particularly suited to treatment of various gastrointestinal conditions in animals, particularly cattle. Such conditions, particularly diarrhea, account for the loss of many calves. Treatment of gastrointestinal conditions is preferably by gastrointestinal administration. In the case of cattle, an effective amount of Elirex™ can be conveniently mixed in with the feed. In humans, administration can be by any method known in the art of gastrointestinal administration. Preferably, administration is oral.

In addition, Elirex™ can be administered to immunodeficient patients, particularly HIV-positive patients, to prevent or at least mitigate apoptotic death of T cells associated with the condition, which results in the exacerbation of immnunodeficiencies as seen in patients with full blown AIDS. Preferably, administration of Elirex™ to such patients is parenterally, but may also be transdermal or gastrointestinally.

The Elirex™ can also be administered to treat apoptosis associated with reperfusion damage involved in a variety of conditions, including, but not limited to, coronary artery obstruction; cerebral infarction; spinal/head trauma and concomitant severe paralysis; reperfusion damage due to other insults such as frostbite; and any indication previously thought to be treatable by superoxide dismutase (SOD). For review of the effect of oxygen radicals in heart disease, see Singal (1988) "Oxygen Radicals in the Pathophysiology of Heart Disease" Kluwer Academic Publishers, Mass., USA.

Myocardial and cerebral infarctions are caused generally by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs in tissue surrounding the infarct upon reperfusion of blood to the area; thus, Elirex™ are effective if administered at the onset of the infarct, during reperfusion, or shortly thereafter.

Thus, the invention includes methods of treating apoptosis associated with reperfusion comprising administering a therapeutically effective amount of Elirex™ to a patient in need of such therapy.

The invention further encompasses a method of reducing the apoptosis and reperfasion damage associated with myocardial and cerebral infarctions for patients with a high risk of heart attack and stroke by administering a therapeutically effective amount of Elirex™ to a patient in need of such therapy.

Preferably, treatment of reperfusion damage is by parenteral administration of the compositions of the invention. Any other suitable method may be used, however, for instance, direct cardiac injection in the case of myocardial infarct. Devices for such injection are known in the art, for instance the Abojcct cardiac syringe.

The invention further provides methods of limiting and preventing apoptosis in cells during the culture or maintenance of mammalian organs, tissues, and cells by the addition of an effective amount of Elirex™ to any media or solutions used in the art of culturing or maintaining mammalian organs, tissues, and cells.

The invention further encompasses media and solutions known in the art of culturing and maintaining mammalian organs, tissues and cells, which comprise an amount of Elirex™ effective to limit or prevent apoptosis of the cells in culture.

These aspects of the invention encompass mammalian cell culture media comprising an effective amount of at least one Elirex™ and the use of such media to limit or prevent apoptosis in mammalian cell culture. An effective amount is one which decreases the rate of apoptosis. Elirex™ have been found to limit or prevent apoptosis under circumstances in which cells are subjected to mild traumas which would normally stimulate apoptosis. Such traumas may include, but are not limited to, low level irradiation, thawing of frozen cell stocks, rapid changes in the temperature, pH, osmolarity, or ion concentration of culture media, prolonged exposure to non-optimal temperature, pH, osmolarity, or ion concentration of the culture media, exposure to cytotoxins, disassociation of cells from an intact tissue in the preparation of primary cell cultures, serum deprivation (or growth in serum-free media).

Thus the invention encompasses compositions comprising tissue culture medium and an effective amount of Elirex™. Serum-free media to which Elirex™ may be added as anti-apoptotic media supplements include, but are not limited to, AIM V® Media, Neuman and Tytell's Serumless Media, Trowell's T8 Media, Waymouth's MB 752/1 and 705/1 Media, and Williams' Media E. In addition to serum-free media, suitable mammalian cell culture media to which Elirex™ may be added as anti-apoptotic media supplements include, but are not limited to, Basal Media Eagle's, Fischer's Media, McCoy's Media, Media 199, RPMI Media 1630 and 1640, Media based on F-10 & F-12 Nutrient Mixtures, Leibovitz's L-15 Media, Glasgow Minimum Essential Media, and Dulbecco's Modified Eagle Media. Mammalian cell culture media to which Elirex™ may be added further comprise any media supplement known in the art, including, but not limited to, sugars, Vitamins, hormones, metalloproteins, antibiotics, antimycotics, growth factors, lipoproteins and sera.

The invention further encompasses solutions for maintaining mammalian organs prior to transplantation, which comprise an effective amount of Elirex™, and the use of such solutions to limit or prevent apoptosis in such mammalian organs during their surgical removal and handling prior to transplantation. In all cases, concentrations of Elirex™ required to limit or prevent apoptosis can be determined empirically by one skilled in the art by methods such as those found in the example provided below, as well as other methods known in the art.

It has now been found that Elirex™ may be topically applied to the skin to treat a variety of dermatologic conditions. These conditions include, but are not limited to, wrinkling or sagging due to age and/or photo damage or psoriasis. The present invention thus encompasses methods of treating dermatological conditions. Furthermore, baldness may be caused by apoptosis of the cells of the hair follicles. Therefore, Elirex™ would be suitable for use in topical treatment of the skin to prevent continued hair loss. Stenn et al. (1994) *J. Invest. Dermatol.* 103:107–111.

As discussed above, these conditions are preferably treated by topical application of a composition comprising an effective amount of Elirex™. An effective amount of Elirex™ is one which ameliorates or diminishes the symptoms of the dermatologic conditions. Preferably, the treatment results in. resolution of the dermatologic condition or restoration of normal skin function; however, any amelioration or lessening of symptoms is encompassed by the invention.

The following examples are provided to illustrate but not limit the invention.

EXAMPLE 1

Synthesis of Reconstituted Optimal Mixture

Commercially available purified soy phospholipids PA, PI, LPA, LPI, LPC (for example, from Avanti® Polar Lipids, Inc.) were suspended in 50 mM ammonium bicarbonate pH 8.0 containing 154 mM NaCl or buffered aqueous solutions free of divalent cations having a pH range of 5 to 8. Total concentrations of phospholipids of greater than 10 mg/ml can be used provided that clarity is obtainable upon sonication. Total concentrations of up to about 50 mg/ml have been utilized.

Typically, the phospholipid mixtures are suspended in a buffer and the mixture is placed in a disposable borosilicate glass, preferably 2–3 ml in a 16×100 mm tube or 1.2 ml in a 13×100 mm tube, or up to 1 ml in a 12×75 mm tube. The combination of phospholipids is then sonicated. Preferably, a small bath sonicator is used, such as a Branson model 200 having an oval bath with dimensions of 9×19 cm, operating at a frequency of 40 kHz with a power consumption of 24 W. The temperature of the water bath is between about 21 and 40° C., preferably between about 25 and 37° C. The water level is adjusted so that it is approximately the same height as the phospholipid mixture in the glass tube(s). Alternatively, a probe sonicator can be used (Fisher Scientific Sonic Dismembrator model 550), as long as care is taken to prevent overheating of the mixture.

The mixture was sonicated for between 3 and 90 minutes, with alternating 5 minute intervals of sonication followed by 5 minutes of equilibration, until the mixture became translucent and passed readily through a filter attached to a 5 ml syringe with a pore size of 0.22 μm.

Figure 1B:
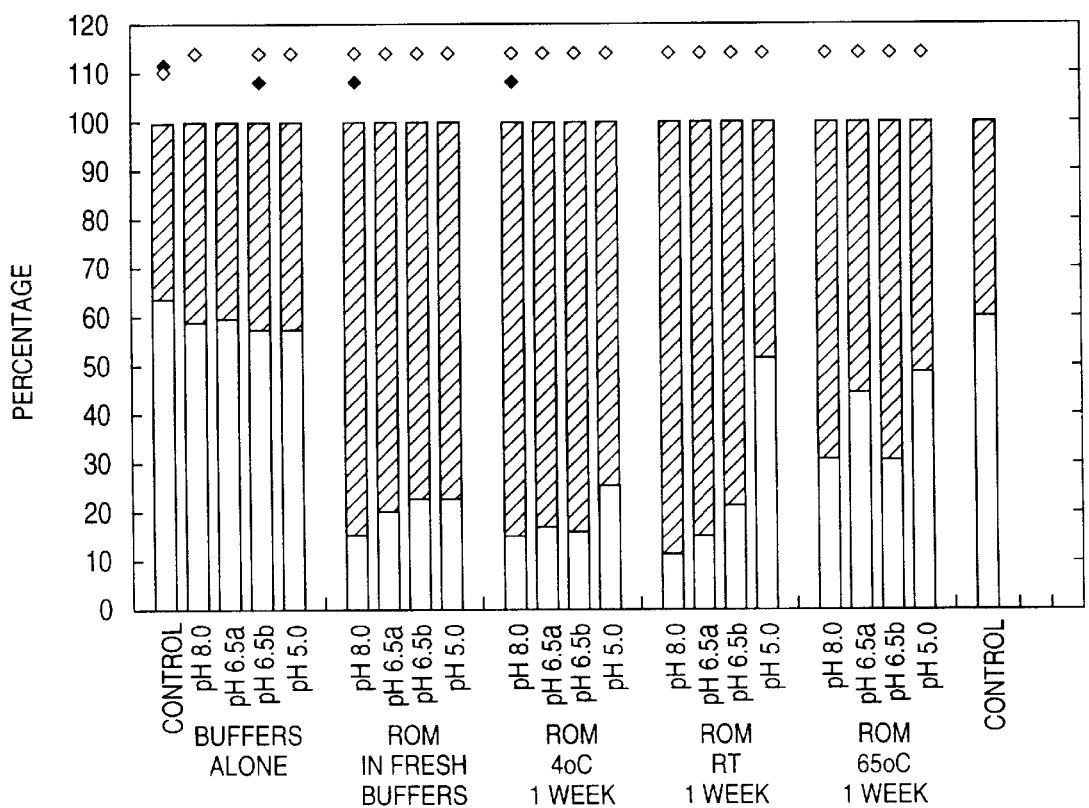
Figure 2A:
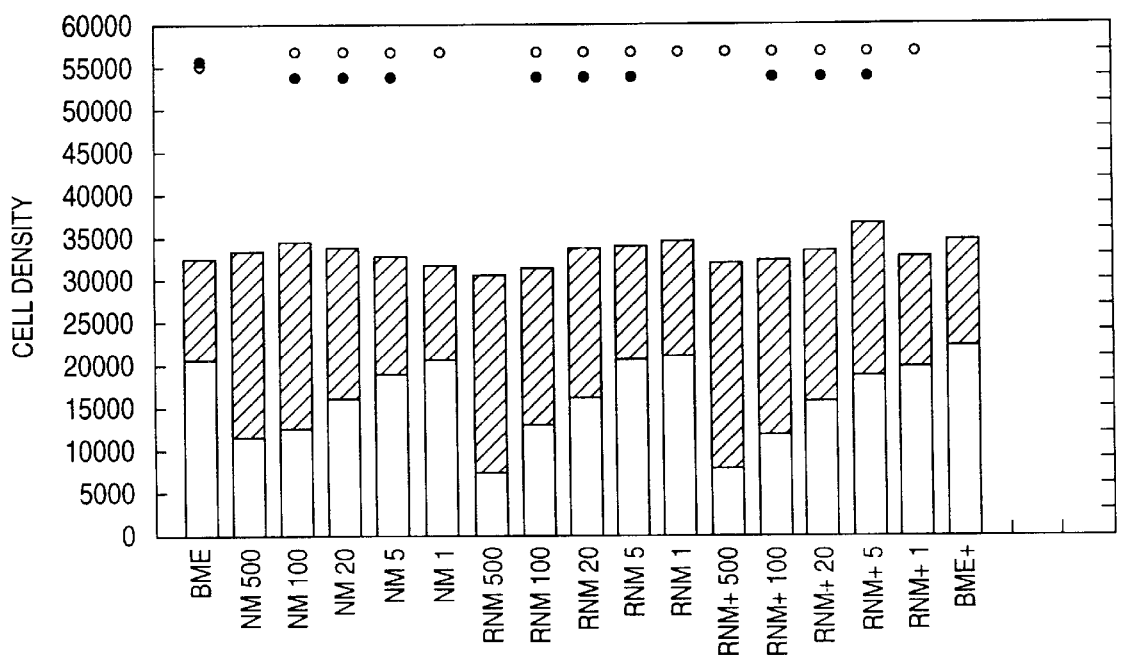
FIGS. 2(A) and 2(B) are bar graphs comparing the anti-apoptotic activity of NM and RNM in 10T 1/2 cells. The hatched portion of the bar represents live cells (ADH). The solid portion of the bar represents apoptotic serum deprived, released cells. NM is a soy-derived extract that exhibits anti-apoptotic activity. RNM is a reconstituted lipid mixture having the ratio of 10:10:2:2:1 (PA:PI:LPA:LPI:LPC). RNM$^+$ is RNM plus bovine serum albumin (BSA) at a final concentration of 0.01%. Anti-apoptotic activity is expressed in terms of cell density (FIG. 2(A)) and percentage (FIG. 2(B)). For FIG. 2(A), open circles denote statistically significant increases in live cells; solid circles denote statistically significant decreases in apoptotic cells. For FIG. 2(B), open diamonds denote statistically significant percentages of cells saved; solid diamonds denote statistically significant percentages of apoptotic cells.
Figure 2B:
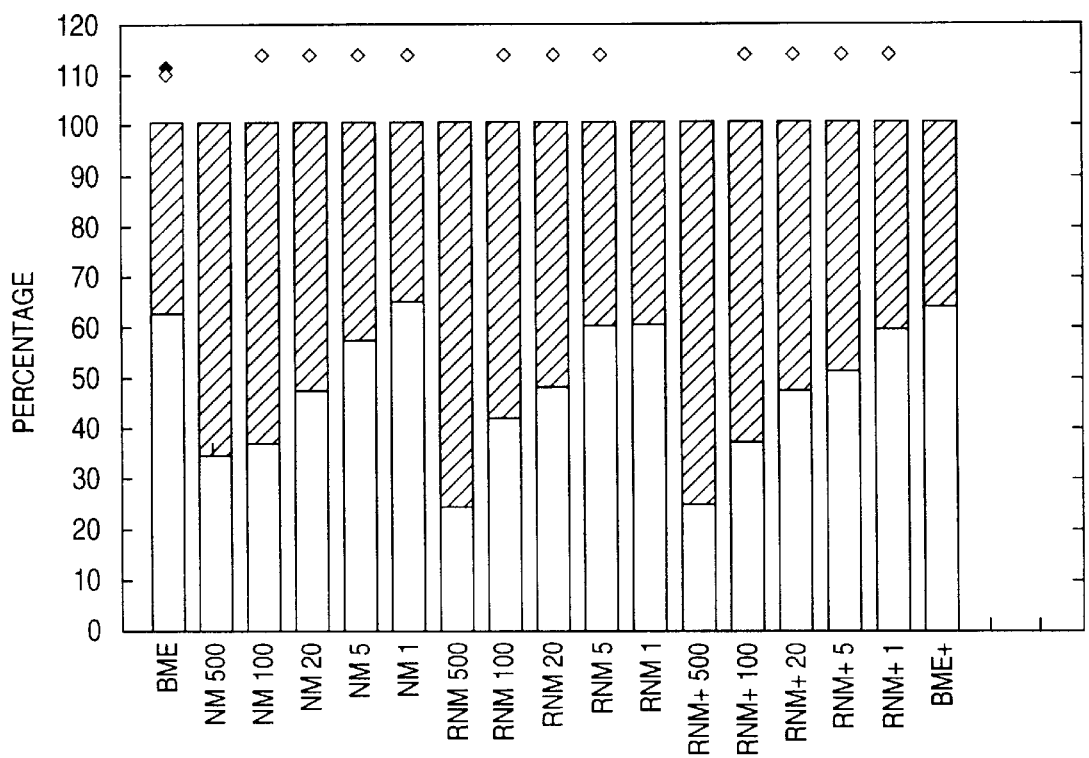
Figure 3A:
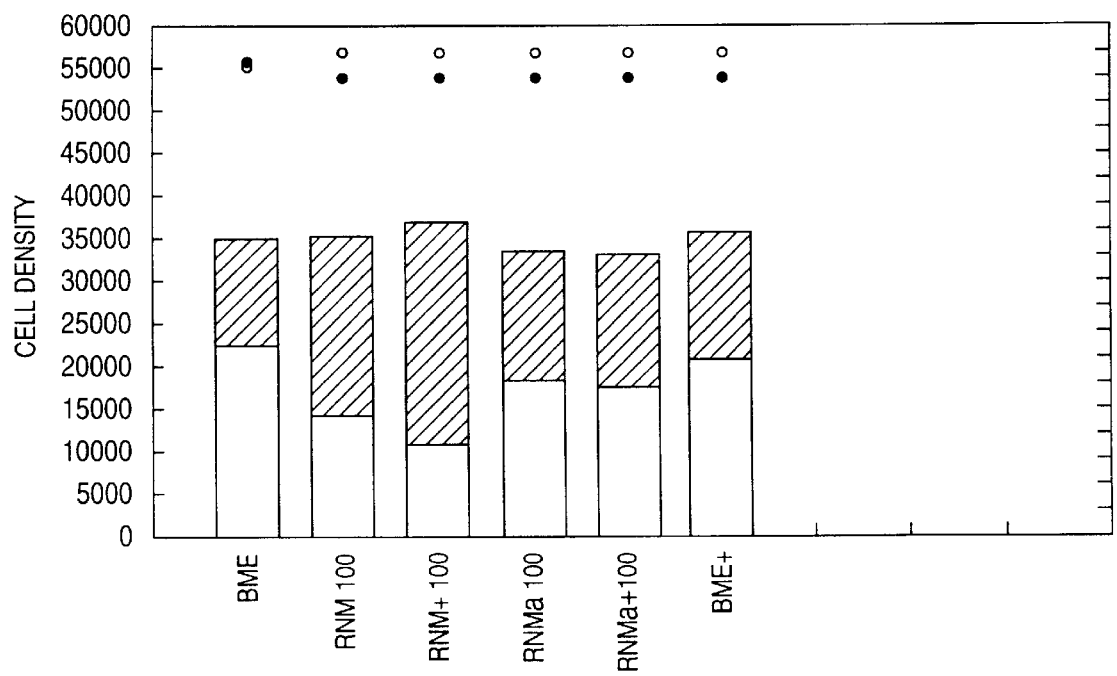
FIGS. 3(A) and 3(B) are bar graphs comparing the anti-apoptotic activity of RNM using plant-derived phospholipids and animal-derived phospholipids. The dose concentration was 100 µg/mL. In the absence or presence of BSA at a final concentration of 0.01%. The hatched portion of the bar represents cells (ADH). The solid portion of the bar represents apoptotic cells (SDR). Anti-apoptotic activity is expressed in terms of cell density (FIG. 3(A)) and percentage (FIG. 3(B)). For each figure, the second and third bars represent soy-derived phospholipids; the fourth and fifth bars represent animal-derived phospholipids. For FIG. 3(A), open circles denote statistically significant increases in live cells (ADH); solid circles denote statistically significant decreases in apoptotic cells (SDR). For FIG. 3(B), open diamonds denote statistically significant percentages of cells saved; solid diamonds denote statistically significant percentages of apoptotic cells.
Figure 3B:
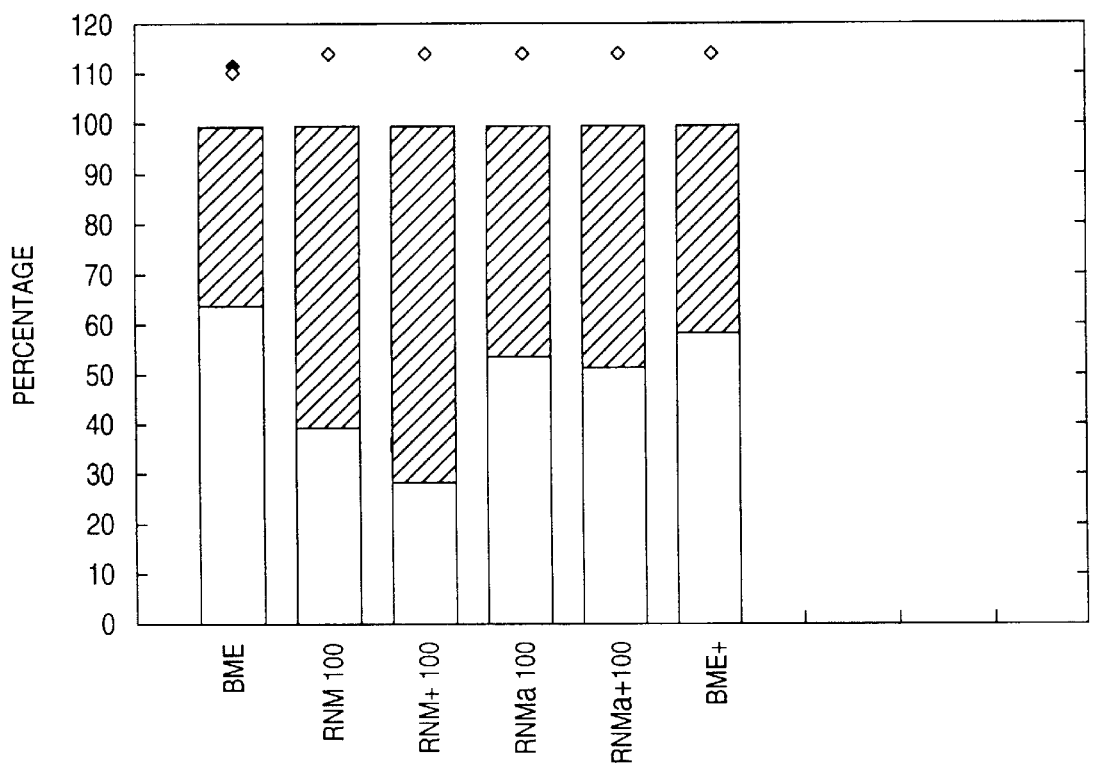
Figure 4A:
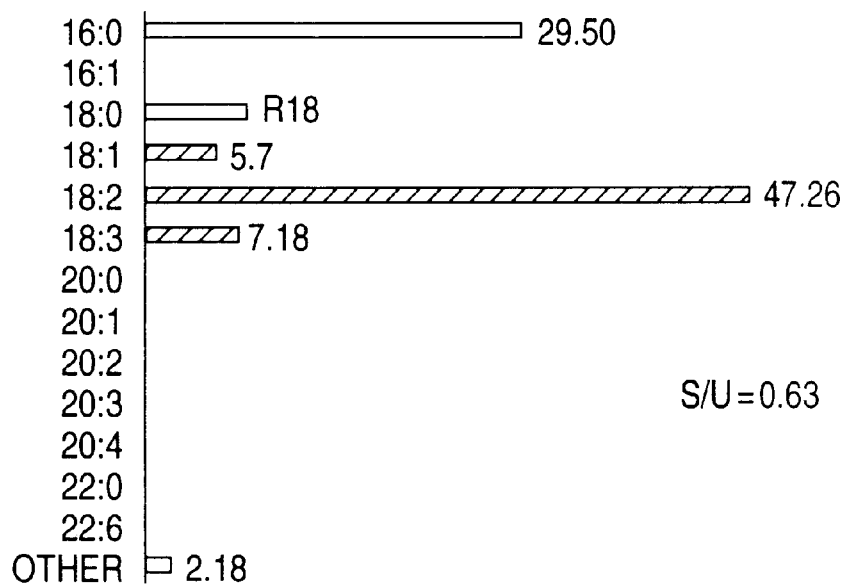
FIG. 4 compares the fatty acid content of soy-derived [A] and bovine liver-derived [B] phospholipids using PI as an example (adapted from Avanti Polar Lipids 1994 catalog). The solid bars represent saturated fatty acids; the hatched bars represent unsaturated fatty acids. Each specie of fatty acid is designated X:Y, with X denoting chain length and Y denoting the number of double bonds. "S/U" refers to the ratio of saturated to unsaturated fatty acids.
Figure 4B:
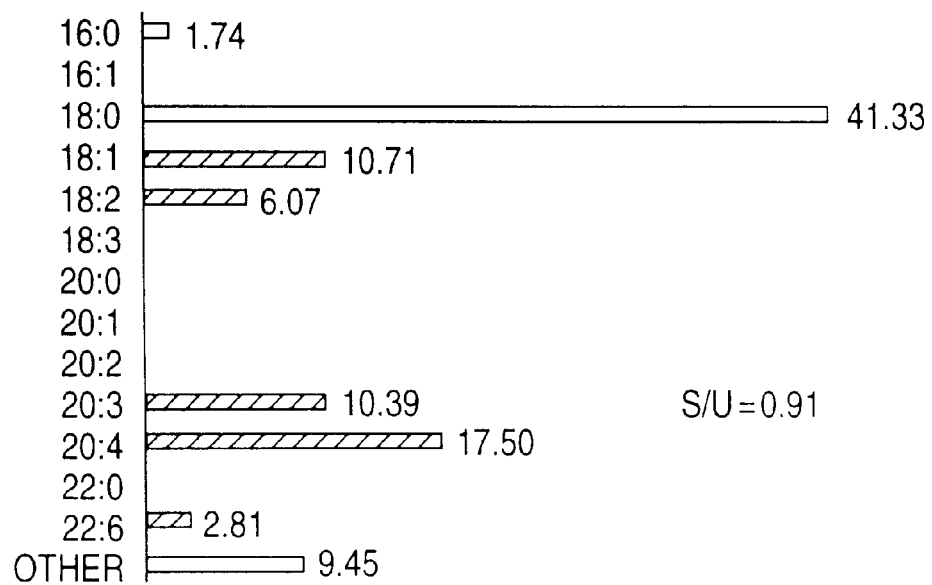
Figure 5A:
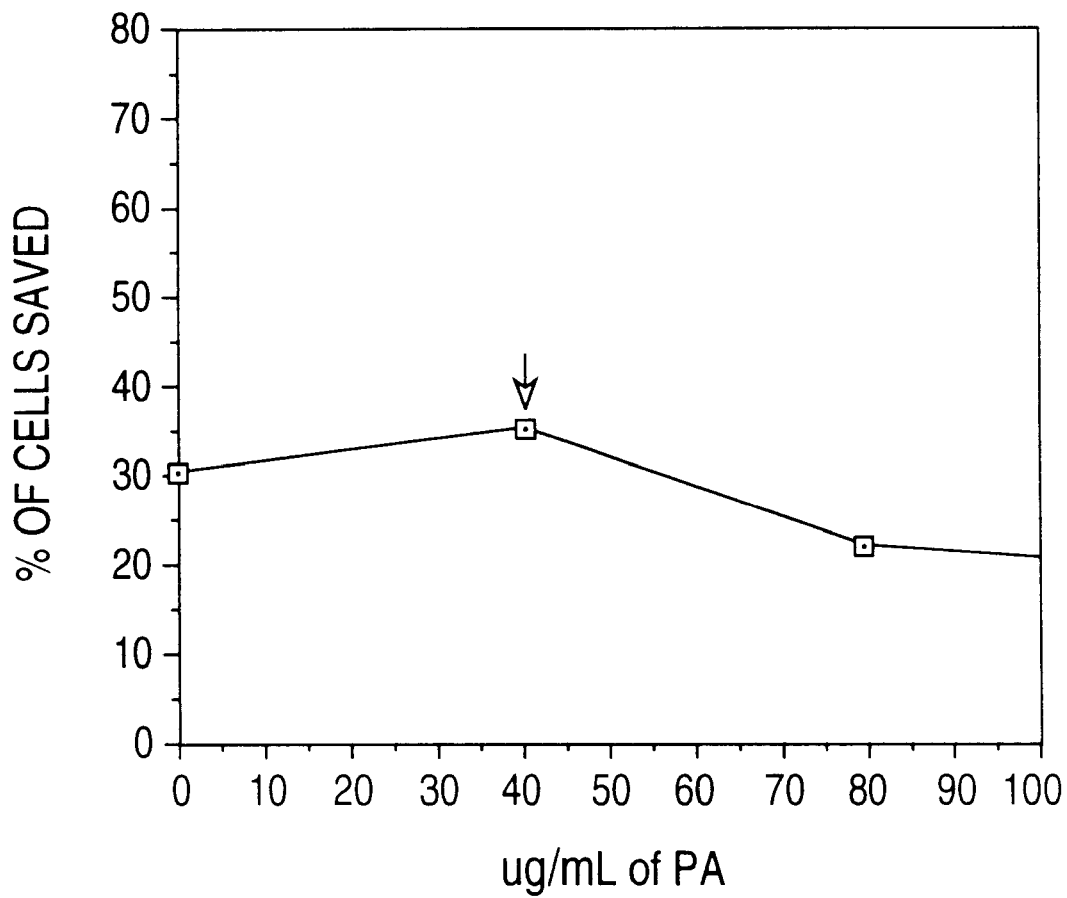
FIGS. 5(A) to (E) are a series of graphs depicting anti-apoptotic activity of PA (FIG. 5(A)), PI (FIG. 5(B)), LPA (FIG. 5(C)), LPI (FIG. 5(D)) and LPC (FIG. 5(E)) at varying concentrations in RNM. The ratio of the remaining phospholipids was held constant at 10:10:2:2:1, (PA:PI:LPA:LPI:LPC) respectively, with varying concentrations (µg/ml) of the phospholipid of interest. Arrows represent the starting concentration of the phospholipid in the 10:10:2:2:1 ratio at a 100 µg/mL dose.
Figure 5B:
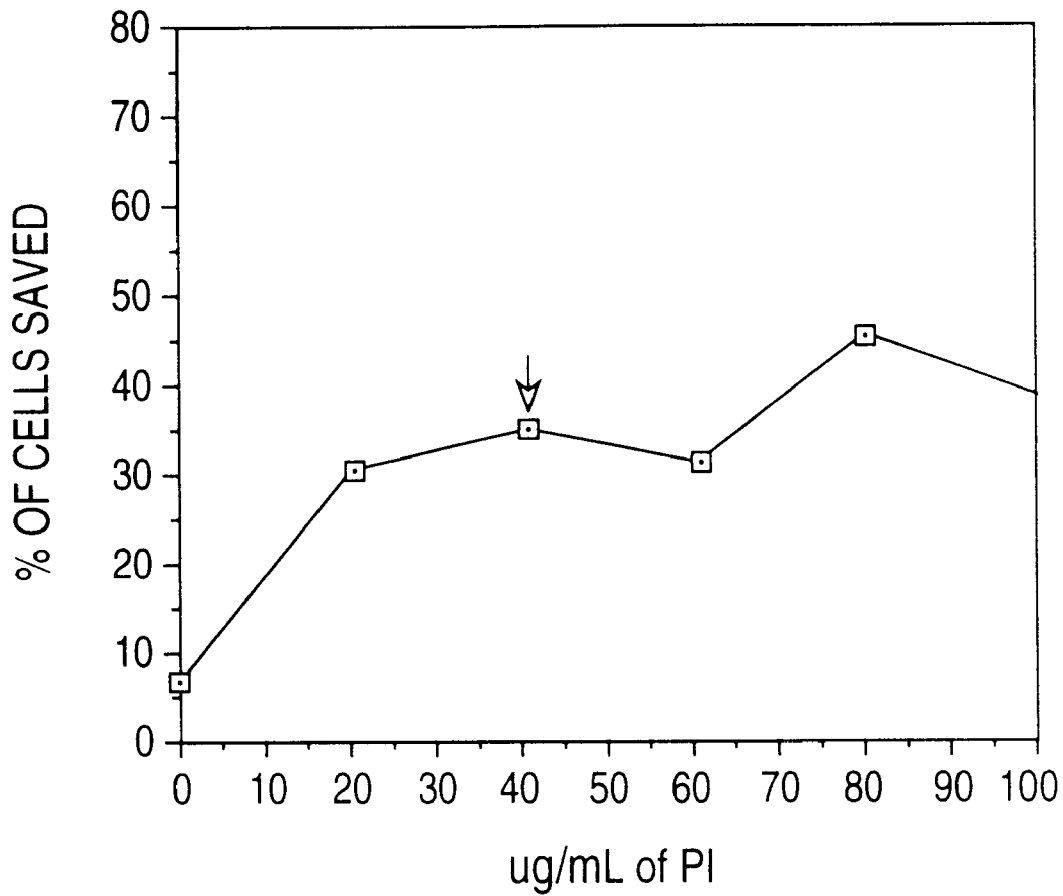
Figure 5C:
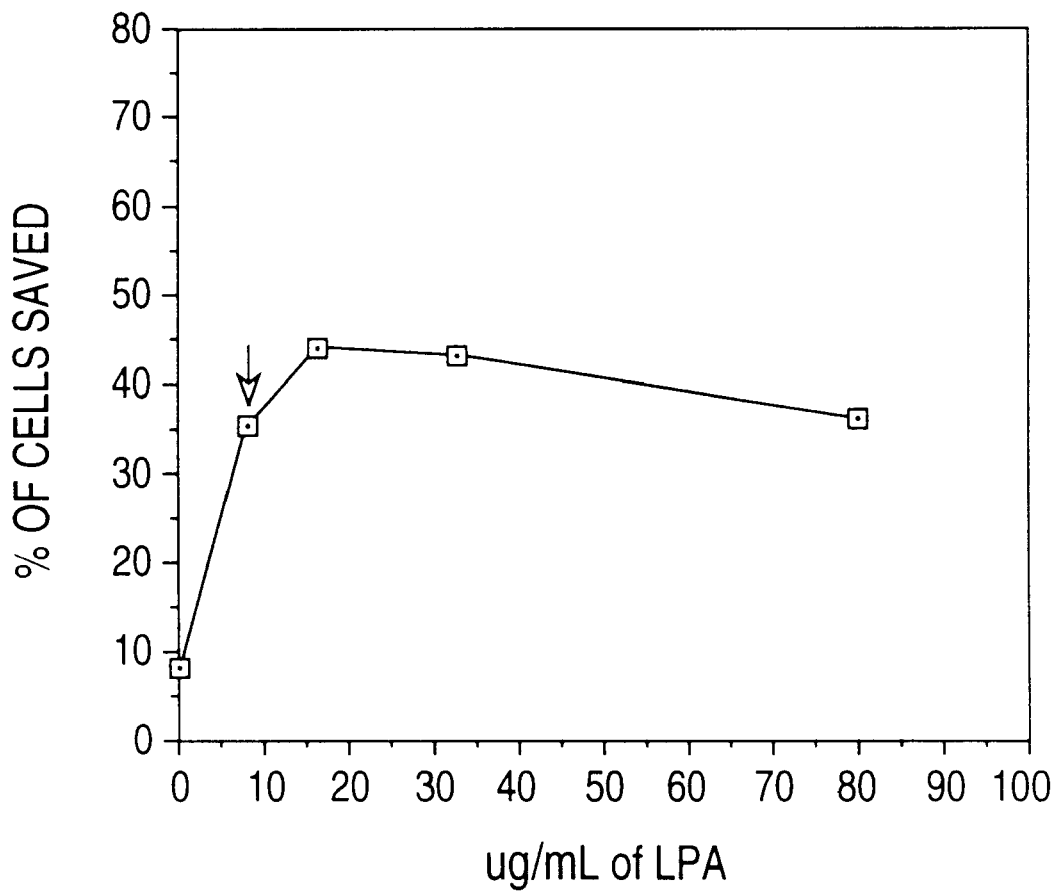
Figure 5D:
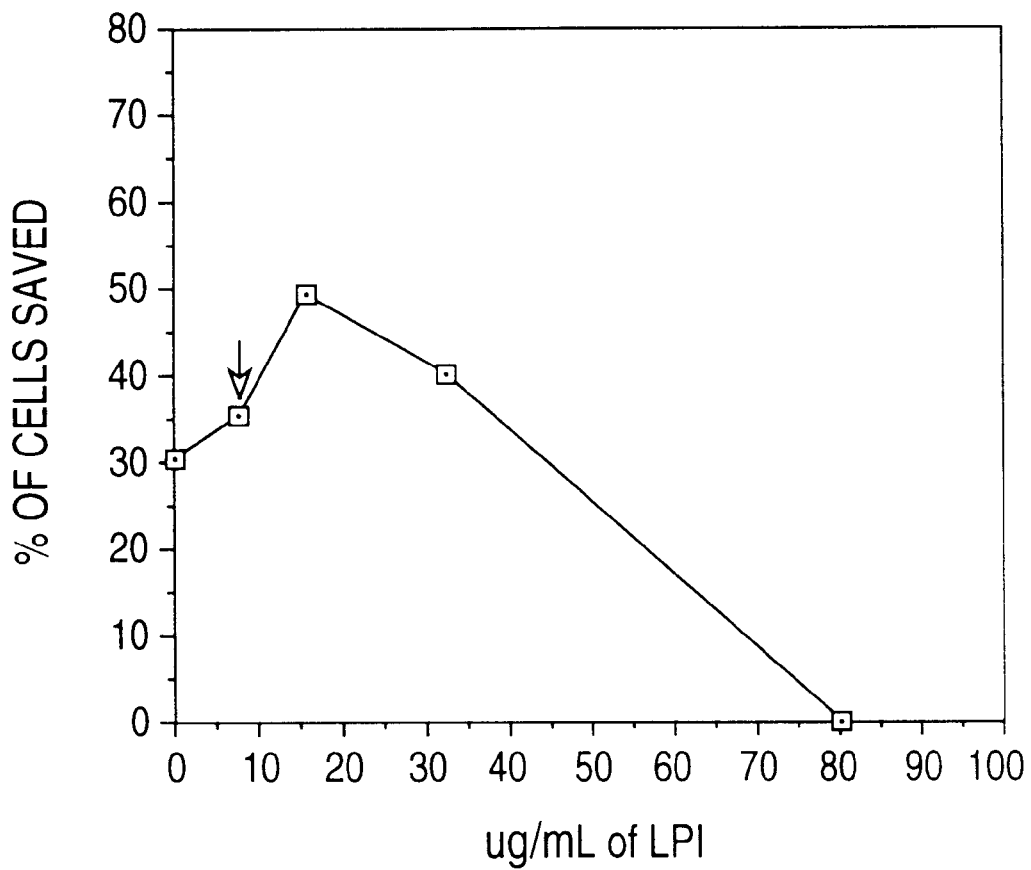
Figure 5E:
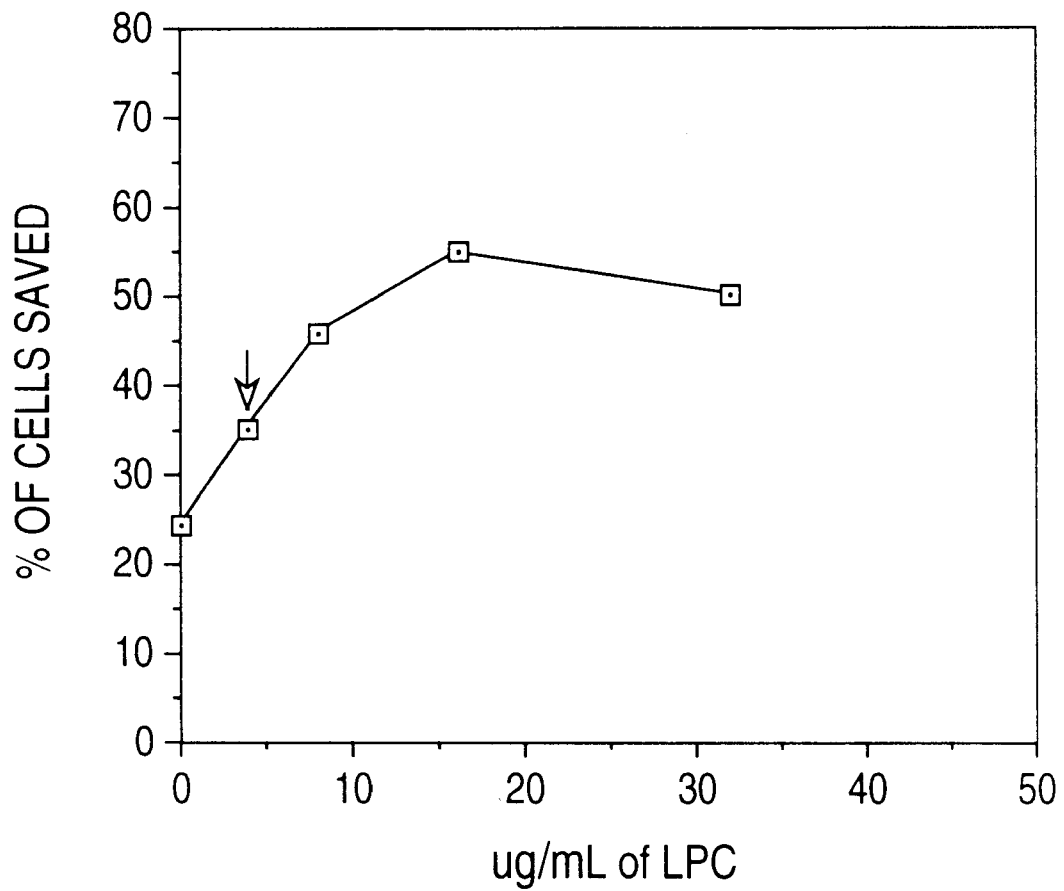

The stability of Elirex™ at various temperature is shown in FIG. 1. Elirex™ were stored for one week at 4° C., room temperature, and 65° C. The results show loss of activity after storage at 65° C., while Elirex™ stored at 4° C. or at room temperature do not have a significant loss of activity.

Optimization of each constituent phospholipid was determined by mixing the purified phospholipids in various ratios, varying one phospholipid at a time. Each mixture was analyzed for anti-apoptotic activity as described in Example 2. When the apparent optimized ratio was obtained, the ratio of the most active ingredient was varied to find the absolute optimized activity. The following Table shows the final ratios tested.

| PA:PI:LPA:LPI:LPC |
|---|
| 10:10:2:2:1 (RNM) |
| 10:10:2:2:2 |
| 10:10:2:2:4 |
| 10:10:4:2:4 |
| 10:10:4:2:1 |
| 10:10:4:2:2 |
| 10:10:8:2:4 (Elirex ™) |

Figure 6:
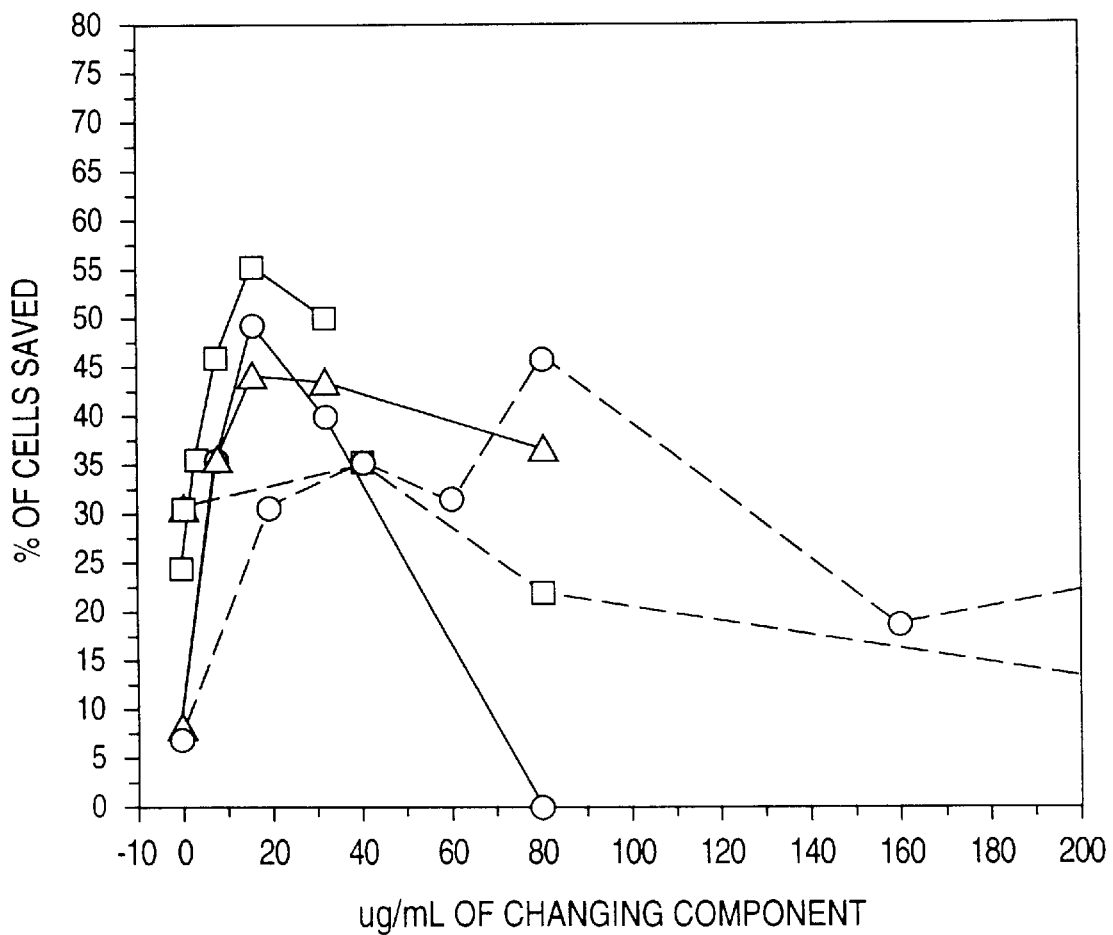
FIG. 6 is a summary graph of the experiments of FIG. 5 depicting the anti-apoptotic activity of each of the phospholipids at varying concentrations. The remaining phospholipids were held at a constant ratio of 10:10:2:2:1 (PA:PI:LPA:LPI:LPC), with varying concentrations (µg/ml) at a 100 µg/mL equivalent dose of the phospholipid of interest. The phospholipids are represented on the graph as follows: LPC (square connected by solid line); LPI (circle connected by solid line); LPA (triangle connected by a solid line); PA (square connected by a dotted line); PI (circle connected by a dotted line).

The results obtained are shown in FIGS. 5–6. The concentration of LPA was varied as was the chain length to determine the effects of these parameters on activity. The stability of Elirex™ at various temperatures is shown in FIG. 1.

EXAMPLE 2

Apoptosis Assay with C3H/10T1/2 Cells

In order to determine the apoptotic activity of Elirex™, the following experiment was performed. The cell assay is described in PCT Publication Nos. WO 94/25621 and WO 95/15173. Briefly, the cells, C3H/10T1/2 clone 8, were assayed at 50–80% confluence, during exponential growth phase when cell cycle position is randomly distributed with no cells arrested in $G_o$, and in quiescence. Exponential growth phase was assured by seeding at 2000 cells per 1 ml (5 ml for a 60 mm culture plate) five days prior to the beginning of the experiment. At T=0, cultures were transferred to serum-free medium, as an apoptosis stimulus, and seed extracts were added. Controls included $10^{-7}$ and $5 \times 10^{-8}$ M 12-O-tetradecanoyl phorbol-13-acetate (TPA) to ensure the responsiveness of the cell culture. The Elirex™ samples were added to serum free medium and sterile filtered prior to addition to the cultures. Assays were performed in triplicate or quadruplicate. Analyses of the cell responses were made between 18 and 28 hours of serum deprivation with or without treatment with Elirex™. Two assays were performed on each cell culture plate consisting of differential cell counts.

1. All non-adherent or loosely adherent cells were removed from the culture dish and counted by appropriate techniques, typically counting by electronic particle counting instrument. These are the apoptotic cells, the serum deprived released cells (SDR), released by the action of cultivation in serum-free medium. Approximately 95% of these released cells are apoptotic as shown by both ultrastructure analysis and DNA fragmentation analysis.

2. The remaining adherent cells (ADH) are exposed to a buffered, typically pH 7.3, balanced salt solution such as Hanks Balanced Salt Solution without calcium and magnesium salts containing 0.05% trypsin and 0.53 mM ethylenediaminetetraacetic acid (EDTA). Each culture is incubated at either room temperature or 37° C. on a rocking platform to ensure uniform distribution of the trypsin reagent over the culture surface. After a standardized period of time, typically 10 minutes, the released cells are removed from each culture dish and measured by the same means as described above, typically electronic particle counting. This ADH cell count is comprised of both trypsin resistant and trypsin sensitive cells as described in PCT Publication No. WO 94/25621.

Anti-apoptotic activity is expressed as the calculated concentration of material (μg/ml of media) required to save 50% of the cells released on serum free treatment.

Figure 7:
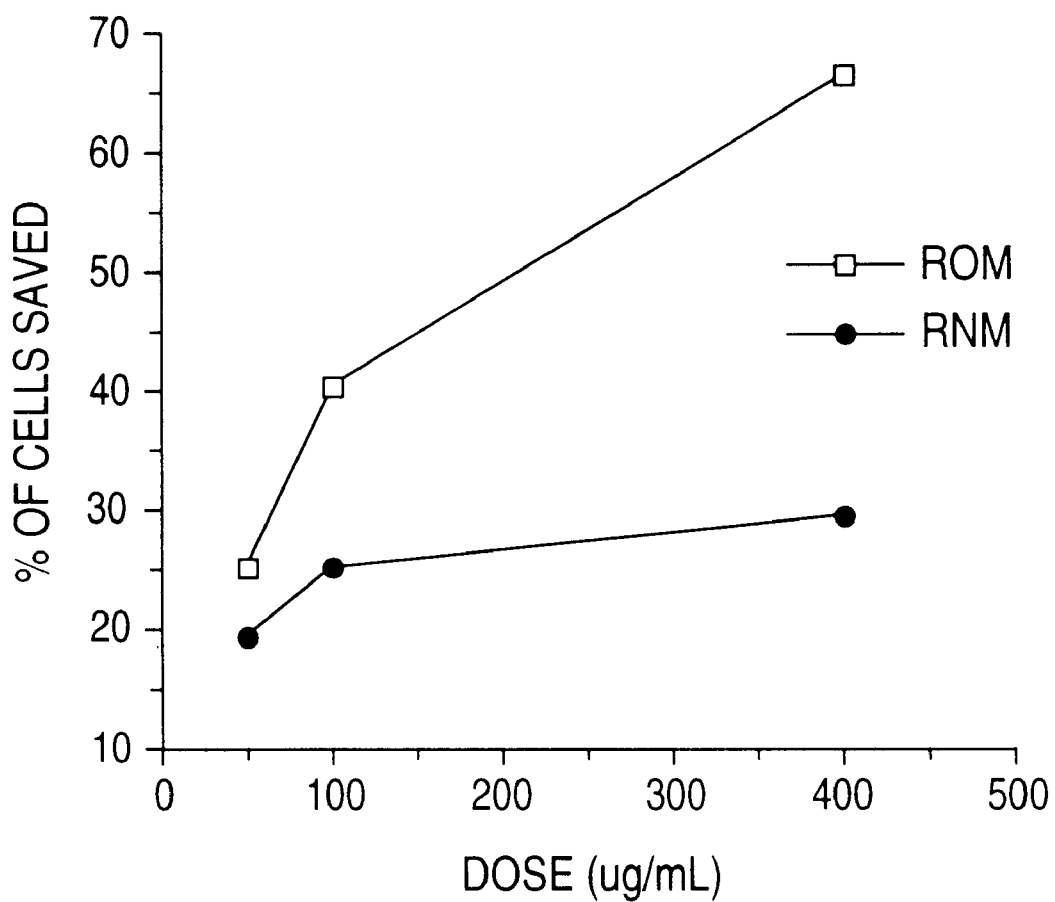
FIG. 7 is a graph comparing anti-apoptotic activity of varying doses of reconstituted RNM and Elirex™. Elirex™ is denoted by open squares connected by a solid line and is the optimized phospholipid ratio derived from FIG. 5 and 6. Anti-apoptotic activity is expressed in terms of percentage of cells saved.
Figure 8:
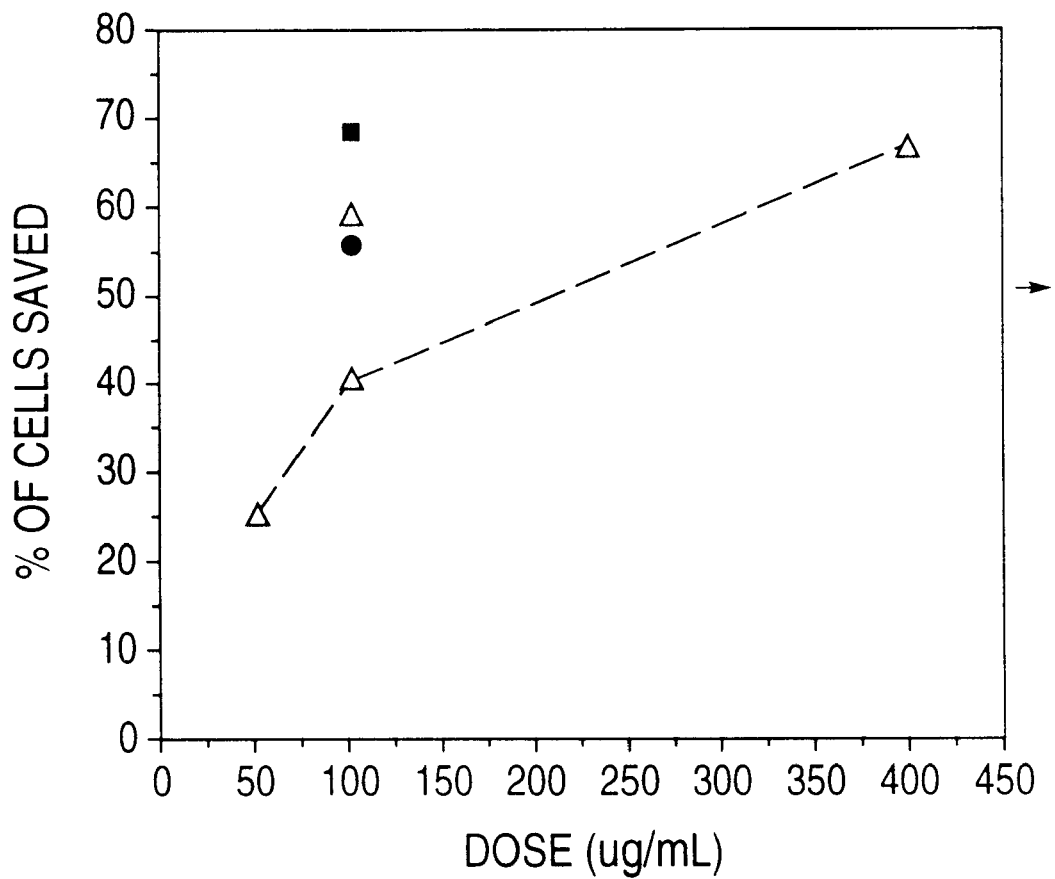
FIG. 8 depicts the anti-apoptotic activity of Elirex™ prepared at various pH levels and diluted into Basal Medium Eagle (BME). The solid triangle connected by a dotted line represents the anti-apoptotic activity of Elirex™ at various concentrations (µg/ml) in BME. The solid square represents the activity of Elirex™ (at 100 µg/ml) at pH 8 (ammonium bicarbonate buffer). The solid triangle represents the activity of Elirex™ at pH 5.0 (sodium acetate buffer). The solid circle represents the activity of Elirex™ at pH 6.5 (sodium phosphate buffer). All were first resuspended with sonication at 10 µg/ml in test buffer containing 100–200 mM NaCl prior to dilution in cell culture media.

The results obtained from the apoptosis cell assays are presented in FIGS. 7–8. In the figures, the percentage of cells having undergone apoptosis (SDR) and adherent cells (ADH) are presented separately. The data in the figures demonstrate that Elirex™ compositions are effective in reducing apoptosis in confluent cells, as compared with the Basal Medium Eagle's (BME), serum-deprived control.

EXAMPLE 3

Anti-apoptotic Activity of Elirex™ as a Function of pH and Salt Concentration The Elirex™ compositions were tested for variance of anti-apoptotic activity at different pH and salt concentrations.

Elirex™ activity was tested by resuspending the phospholipids as described in Example 1 in ammonium bicarbonate pH 8.0, or sodium phosphate pH 6.5, or HEPES pH 6.5, or sodium acetate pH 5.0, all at 50 mM in the presence of sodium chloride at 154 mM (isotonic). The results obtained are presented in FIG. 1. pH 8 appears to give the best activity.

In order to test the effect of salt concentration the pH 8 solution was tested at 0, 100, 500 and 1000 mM sodium chloride concentration. All of the samples were prepared as concentrated solutions and diluted with BME for treating the cells. The optimum salt concentration was found to be between 100 and 200 mM, the results are not depicted.

Storage stability at various temperatures was also tested. All the solutions were stored at 4, 37 and 60° C. for one week and tested for activity. The results obtained are depicted in FIG. 1.

The optimum solution was found to be 104 mM sodium chloride in 50 mM ammonium bicarbonate at pH 8, stored at 4° C.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

We claim:

1. A composition with anti-apoptotic activity consisting essentially of:
   (a) phosphatidic acid (PA);
   (b) phophatidylinositol (PI);
   (c) lysophosphatidic acid (LPA);
   (d) lysophosphatidylinositol (LPI); and
   (e) lysophosphatidylcholine (LPC)
wherein the phospholipids are substantially pure and wherein the pbosoholipids are present in a ratio of from about 2.8:6:2:2 to 15:15:10:4:8.

2. The composition according to claim 1, wherein the phospholipids are present in a ratio of from about 4:16:12:4:4 to 7.5:7.5:5:2:4.

3. The composition according to claim 1, wherein the phospholipids are present in a ratio of from about 10:10:8:2:4, respectively.

4. The composition according to claim 1 wherein the phospholipids are derived from a plant, animal or synthetic source, wherein LPA is not derived from an animal source.

5. The composition according to claim 4, wherein the phospholipids derived from an animal are derived from liver.

6. The composition according to claim 1, wherein the composition has been sonicated.

7. The composition of claim 6, wherein the sonication occurs until the composition is translucent.

8. The composition of claim 6, wherein the sonication is for about 3 minutes to about 90 minutes.

9. The composition according to claim 6, wherein the sonication occurs in alternate 5 minute periods of sonication and equilibration.

10. The composition according to claim 6, wherein the sonication occurs such that the temperature of the composition does not exceed about 60° C.

11. The composition according to claim 1, further comprising a physiologically acceptable buffer.

12. The composition according to claim 11, wherein the buffer has a pH of about 5.5–8.0.

13. The composition according to claim 12, wherein the buffer has a pH of about 8.0.

14. The composition according to claim 1, wherein the phospholipids are present in a total concentration of about 10 mg/ml.

15. A method of obtaining a composition with anti-apoptotic activity comprising the steps of:
   (a) combining an amount of:
      (i) phosphatidic acid (PA),
      (ii) phosphatidylinositol (PI),
      (iii) lysophosphatidic acid (LPA),
      (iv) lysophosphatidylinositol (LPI), and
      (v) lysophosphatidylcholine (LPC)
   effective to produce a ratio of from. about 2:8:6:2:2 to 15:15:10:4:8 with anti-apoptotic activity in a physiologically acceptable buffer; and
   (b) sonicating the phospholipid/buffer mixture.

16. The method according to claim 15 wherein the phospholipids are derived from a plant, animal or synthetic source wherein LPA is not derived from an animal source.

17. The method according to claim 16, wherein the phospholipids derived from an animal are derived from liver.

18. The method according to claim 16, wherein the phospholipids are present in a total concentration of about 10 mg/ml.

19. The method according to claim 15, wherein the sonication occurs until the combination of phospholipids becomes translucent.

20. The method according to claim 15, wherein the sonication is for about 3 minutes to about 90 minutes.

21. The method according to claim 15, wherein the sonication occurs in alternate 5 minute periods of sonication and equilibration.

22. The method according to claim 15, wherein the sonication occurs such that the temperature of the composition does not exceed 60° C.

23. The method of claim 15 wherein the buffer has a pH of about 8.0.

24. The method of claim 23 wherein the buffer is selected from the group consisting of bicarbonate.

25. A composition obtained according to the method of claim 15, 19 or 21.

26. A method of treatment of apoptosis, comprising administering a therapeutically effective amount of a pharmaceutically acceptable composition comprising the composition according to claim 25 to a patient in need of such treatment.

27. The method according to claim 26, wherein the patient is suffering from a gastrointestinal perturbation.

28. The method according to claim 27, wherein the gastrointestinal perturbation is caused by a stimulus selected from the group consisting of human immunodeficiency virus, chemotherapeutic agents and radiation and those associated with infectious diseases.

29. The method according to claim 27, wherein the gastrointestinal perturbation is due to inflammatory bowel disease.

30. The method according to claim 28, wherein the infectious disease is selected from the group consisting of diarrhea-causing organisms.

31. The method according to claim 29, wherein the treatment decreases immunodeficiencies associated with immunosuppressing viruses, chemotherapeutic agents, or radiation and immunosuppressive drugs.

32. The method according to claim 31, wherein the virus is human immunodeficiency virus.

33. The method according to claim 26, wherein the patient is undergoing apoptosis related to ischemia and/or reperfiasion subsequent to ischemia.

34. The method according to claim 33, wherein the reperfusion is associated with coronary artery obstruction; cerebral infarction; spinal/head trauma and concomitant severe paralysis and frostbite.

35. A composition comprising a tissue culture media and an effective amount of a composition according to claim 25.

36. The method of preventing apoptosis in cultured cells comprising treating cells with a composition according to claim 35.

37. The method according to claim 36, wherein the cells are mammalian.

38. The method according to claim 37, wherein the cells are human.

39. The method according to claim 36, wherein the cells are insect.

40. The method according to claim 37, wherein the cells are part of a tissue or organ.

41. A method of organ preservation comprising adding an effective amount of the composition of claim 25 to the solution in which the organ is stored.

42. A method of organ preservation comprising administering to the host animal at least one intravenous bolus of an effective amount of the composition of claim 25.

43. A method of treating dermatologic conditions in which apoptosis is implicated, comprising topically administering a therapeutically effective amount of a pharmaceutically acceptable composition comprising the composition according to claim 25 to a patient in need of such treatment.

44. The method according to claim 43, wherein the dermatological condition is wrinkling, sagging, psoriasis, baldness or hair loss.

45. The method according to claim 44, wherein the composition of claim 25 is in a cream or ointment or gel.

46. A method of treating wounds comprising administering an effective amount of the composition of claim 25.

* * * * *